(12) United States Patent
Nobis et al.

(10) Patent No.: US 6,605,098 B2
(45) Date of Patent: Aug. 12, 2003

(54) SURGICAL DEVICE FOR CREATING AN ANASTOMOSIS BETWEEN FIRST AND SECOND HOLLOW ORGANS

(75) Inventors: Rudolph H. Nobis, Mason, OH (US); Christopher J. Hess, Lebanon, OH (US); Gary W. Knight, West Chester, OH (US); Michael F. Clem, Maineville, OH (US); Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 41 days.

(21) Appl. No.: 09/967,227

(22) Filed: Sep. 28, 2001

(65) Prior Publication Data

US 2003/0065342 A1 Apr. 3, 2003

(51) Int. Cl.[7] ............................................... A61B 17/08
(52) U.S. Cl. ...................................... 606/153; 606/185
(58) Field of Search ............................... 606/153, 184, 606/185, 167

(56) References Cited

U.S. PATENT DOCUMENTS

| | | | |
|---|---|---|---|
| 4,366,819 A | 1/1983 | Kaster | |
| 5,234,447 A | 8/1993 | Kaster et al. | |
| 5,676,670 A | 10/1997 | Kim | |
| 5,702,412 A | 12/1997 | Popov et al. | |
| 5,797,920 A | 8/1998 | Kim | |
| 5,797,933 A | 8/1998 | Snow et al. | |
| 5,797,934 A | 8/1998 | Rygaard | |
| 5,817,113 A | 10/1998 | Gifford, III et al. | |
| 5,833,698 A | 11/1998 | Hinchliffe et al. | |
| 6,024,748 A | * 2/2000 | Manzo et al. | 606/153 |
| 6,471,713 B1 | * 10/2002 | Vargas et al. | 606/153 |

FOREIGN PATENT DOCUMENTS

| | | |
|---|---|---|
| WO | WO 97/13463 | 4/1997 |
| WO | WO 97/13471 | 4/1997 |
| WO | WO 97/27898 | 8/1997 |
| WO | WO 97/28749 | 8/1997 |
| WO | WO 97/40754 | 11/1997 |
| WO | WO 98/38922 | 9/1998 |
| WO | WO 98/38939 | 9/1998 |
| WO | WO 98/38941 | 9/1998 |
| WO | WO 98/38942 | 9/1998 |
| WO | WO 98/42262 | 10/1998 |
| WO | WO 99/62415 | 12/1999 |

* cited by examiner

*Primary Examiner*—Julian Woo

(57) ABSTRACT

A surgical device including: a punch slidingly disposed in a housing for forming a hole in a first vessel; a cartridge movably disposed in the housing between a cutting and deploying positions, the cartridge having a second vessel and a coupler for coupling the first and second vessel loaded therein; a punch actuator for sliding the punch between the cutting and deploying positions; a cartridge actuator for moving the cartridge between the cutting and deploying positions, wherein while in the cutting position, the punch and cartridge are in position to permit the punch to form the hole in the first vessel and while in the deploying position, they are in position to deploy the second vessel; and a deployment mechanism for deploying the second vessel and coupler into the hole of the first vessel while the punch and cartridge are in the deploying position to create an anastomosis.

31 Claims, 30 Drawing Sheets

SURGICAL DEVICE FOR CREATING AN ANASTOMOSIS BETWEEN FIRST AND SECOND HOLLOW ORGANS

BACKGROUND OF THE INVENTION

1. Field of the Invention

The present invention relates generally to surgical devices, and more particularly, to a surgical device for creating an anastomosis between first and second hollow organs, preferably between the aorta and a harvested vessel.

2. Prior Art

To perform a coronary artery bypass graft (CABG), a cardiac surgeon traditionally hand sutures the proximal and distal ends of the harvested graft vessel, which is usually a portion of the saphenous vein or radial artery. The proximal end attaches to the patient's aorta and the distal end attaches to the diseased coronary artery, bypassing the blockage. Hand suturing the graft vessel is a time consuming procedure requiring great surgical skill, and typically requires a sternotomy or thoracotomy for access to the surgical site. Anastomosis devices have been developed which comprise a handle, which is interchangeably used with a hole puncher for creating the aortotomy, and a delivery device that is supplied with the anastomotic coupler and that must be "loaded" with the graft vessel prior to deployment of the vessel and coupler to the aorta. The delivery device is approximately 30 cm long and has controls for deploying the coupler and the vessel. Because of the size of these devices, cardiac surgeons may prefer to perform the proximal anastomosis to the aorta prior to the distal anastomosis to the coronary artery on the heart. Surgeons prefer this order so that loading of the vessel into the delivery device, and subsequent manipulation of the device while performing the proximal anastomosis, is not hampered by the vessel graft (only about 12–20 cm long) being already attached on its distal end to the heart.

These anastomosis devices generally have different sizes of anastomotic couplers (for differently sized graft vessels), each of which is supplied to the user in an appropriately labeled delivery device. If the surgeon should decide to open the sterile package for the delivery device containing the first size and then decides to change to the second size, or if the first device is unintentionally rendered inoperable due to misleading, etc., then the entire first device must be discarded. Also the surgeon may need to perform multiple bypasses when two or more graft vessels are anastomosed to the aorta.

The anastomosis devices of the prior art also require that the operator first assemble the punch with the handle in order to create the aortotomy. Next the punch must be removed from the handle while the distal end of the handle is held steadily in the aortotomy to prevent leakage of blood. While still holding the handle with the distal end in the aortotomy, the operator assembles the delivery device, already loaded with a graft vessel and the anastomotic coupler, into the handle. The surgeon must exchange these instrument components within the surgical opening providing access to the aorta resulting in a leakage of blood from the aorta.

SUMMARY OF THE INVENTION

Therefore it is an object of the present invention to provide a surgical device for creating an anastomosis between first and second hollow organs that allows a distal anastomosis to be more easily performed first before a proximal anastomosis, in case this is the surgeon's preference.

It is another object of the present invention to provide a surgical device for creating an anastomosis between first and second hollow organs which has a relatively low cost component that is separate from the delivery device, contains the anastomotic coupler, and may be loaded with the graft vessel.

It is yet another object of the present invention to provide a surgical device for creating an anastomosis between first and second hollow organs wherein the remainder of the device (other than the component discussed immediately above) is reloadable and has controls that may be reset for multiple use.

It is still another object of the present invention to provide a surgical device for creating an anastomosis between first and second hollow organs, which minimizes blood leakage and/or injury to the hollow organs.

It is still another object of the present invention to provide a surgical device for creating an anastomosis between first and second hollow organs, which eliminates instrument exchanges.

Accordingly, a surgical device for creating an anastomosis between first and second hollow organs is provided. The device comprises: a housing; a punch slidingly disposed in the housing for forming a hole in the first hollow organ; a cartridge movably disposed in the housing between a cutting position and a deploying position, the cartridge having the second hollow organ and a coupler for coupling the first and second hollow organs loaded therein; punch actuation means for sliding the punch between the cutting and deploying positions, wherein while in the cutting position the punch is in position to form the hole in the first hollow organ and while in the deploying position, the punch is in position to permit the deployment of the second hollow organ; cartridge actuation means for moving the cartridge between the cutting and deploying positions, wherein while in the cutting position, the cartridge is in position to permit the punch to form the hole in the first hollow organ and while in the deploying position, the cartridge is in position to deploy the second hollow organ; and deploying means for deploying the second hollow organ and coupler into the hole while the punch and cartridge are in the deploying position to create the anastomosis.

The first hollow organ is preferably the aorta of the heart and the second hollow organ is preferably a harvested vessel. The coupler is preferably an anastomotic device having a set of pins on each of two ends, one of the sets of pins coupling the anastomotic device to a distal end of the second hollow organ and the other set of pins coupling the anastomotic device to a wall of the second hollow organ about the hole.

Preferably, the surgical device for creating an anastomosis between first and second hollow organs comprises: a housing; a punch slidingly disposed in the housing along a central axis for forming a hole in the first hollow organ; a cartridge movably disposed in the housing between a position offset from the central axis and a position aligned with the central axis, the cartridge having the second hollow organ and a coupler for coupling the first and second hollow organs loaded therein; punch actuation means for sliding the punch between cutting and deploying positions, wherein while in the cutting position the punch is in position to form the hole in the first hollow organ and while in the deploying position, the punch is in position to permit the deployment of the second hollow organ; cartridge actuation means for moving the cartridge between the cutting and deploying positions, wherein while in the cutting position the cartridge is in the position offset from the central axis and while in the deploying position, the cartridge is in the position aligned with the central axis; and deploying means for deploying the second hollow organ and coupler into the hole while the punch and cartridge are in the deploying position to create the anastomosis.

More preferably, the cartridge is rotatably disposed in the housing and the cartridge actuation means comprises; a cradle rotatably disposed in the housing for accepting the cartridge; and a shaft connected to the housing upon which the cradle rotates.

Preferably, the punch comprises: a shaft disposed along the central axis; and a punch tip disposed at a distal portion of the shaft and having a pointed surface for piercing the first hollow organ. More preferably, the punch further comprises means for retracting the pointed surface of the punch tip into a lumen of the shaft. Furthermore, the punch tip preferably has a proximal edge for cutting a wall of the first hollow organ, a grooved portion proximate to the punch tip for capturing a wall of the first hollow organ, and means for retracting the punch tip to sandwich the wall between the proximal edge and a portion of the housing and to sever the wall around a periphery of the proximal edge.

The cartridge preferably further comprises a seal for sealing liquid in the first internal organ from entering the device. The cartridge further preferably comprises a splitting means for splitting the cartridge and seal subsequent to deployment of the second hollow organ and coupler for facilitating release of the second hollow organ from the device. The coupler preferably has pins for securing the second hollow organ to the hole of the first hollow organ, the pins being biased in a bent position, where the cartridge further comprises retaining means for retaining the pins in a substantially straight position prior to deployment of the second hollow organ and coupler. In which case the deploying means preferably comprises; means for pushing a distal end of the second hollow organ and the coupler into the hole of the first hollow organ; and means for releasing the restraint on the pins thereby fixing the second hollow organ to the hole of the first hollow organ. The means for pushing the distal end of the second hollow organ and coupler into the hole of the first hollow organ preferably comprises a shaft operatively connected to the cartridge for sliding the cartridge along the central axis such that the distal end of the second hollow organ protrudes from the housing and into the hole of the first hollow organ. The means for releasing the restraint on the pins preferably comprises: a screw tube rotatably disposed in the housing and operatively connected to the cartridge; a knob connected to a distal end of the screw tube, wherein rotation of the knob releases the restraint on the pins.

The punch actuation means preferably comprises: a punch lever rotatably disposed on a shaft of the punch, wherein pulling the punch lever in the proximal direction moves the punch from the cutting position to the deploying position; and retainer means for retaining the punch lever in the housing as it is pulled in the proximal direction. Furthermore, the cartridge and punch actuation means preferably also comprise locking means for locking the cartridge, punch lever and punch in the deploying position.

Also provided is a method for creating an anastomosis between first and second hollow organs. The method comprising: providing a punch slidingly disposed in a housing along a central axis; providing a cartridge movably disposed in the housing between a position offset from the central axis and a position aligned with the central axis; loading the second hollow organ and a coupler for coupling the first and second hollow organs into the cartridge; sliding the punch distally to create a hole in a wall of the first hollow organ; sliding the punch proximally to provide clearance for rotation of the cartridge into the position aligned with the central axis; moving the cartridge from the axis offset from the central axis to the position aligned with the central axis; and deploying the second hollow organ and coupler into the hole to create the anastomosis.

The punch preferably comprises a shaft disposed along the central axis; and a punch tip disposed at a distal portion of the shaft and having a pointed surface for piercing the first hollow organ, in which case the method further comprises retracting the pointed surface of the punch tip into a lumen of the shaft. Preferably, the punch tip has a proximal edge for cutting the wall of the first hollow organ and a grooved portion proximate to the punch tip, in which case the method further comprises: capturing the wall of the first hollow organ in the grooved portion; and retracting the punch tip to sandwich the wall between the proximal edge and a portion of the housing to sever the wall around a periphery of the proximal edge.

Preferably, the method further comprises sealing liquid in the first internal organ from entering the device and splitting the cartridge and seal subsequent to deployment of the second hollow organ and coupler for facilitating release of the second hollow organ from the device.

The coupler preferably has pins for securing the second hollow organ to the hole of the first hollow organ, the pins being biased in a bent position, in which case the method further comprises retaining the pins in a substantially straight position prior to deployment of the second hollow organ and coupler. The method also preferably further comprises; pushing a distal end of the second hollow organ and the coupler into the hole of the first hollow organ; and releasing the restraint on the pins thereby fixing the second hollow organ to the hole of the first hollow organ. Preferably, a screw tube is rotatably disposed in the housing and operatively connected to the cartridge, wherein the releasing comprises rotating a knob connected to a distal end of a screw tube to release the restraint on the pins. Preferably, the method also further comprises restraining the rotation of the knob in the direction that releases the restraint on the pins and releasing the restraint and allowing the knob to be reset to an initial position for subsequent operations of the device.

BRIEF DESCRIPTION OF THE DRAWINGS

These and other features, aspects, and advantages of the apparatus and methods of the present invention will become better understood with regard to the following description, appended claims, and accompanying drawings where:

FIG. 4b illustrates a cross sectional view of the vessel cartridge of FIG. 4a.

FIG. 5b illustrates a section view corresponding to the proximal end of the surgical device of FIG. 5a.

DETAILED DESCRIPTION OF THE PREFERRED EMBODIMENT

Although this invention is applicable to numerous and various types of hollow organs, it has been found particularly useful in the environment of CABG to create an anastomosis between the aorta and a harvested vessel, such as a saphenous vein or radial artery. Therefore, without limiting the applicability of the invention to the environment of CABG to create an anastomosis between the aorta and a harvested vessel, the invention will be described in such environment.

Figure 1:
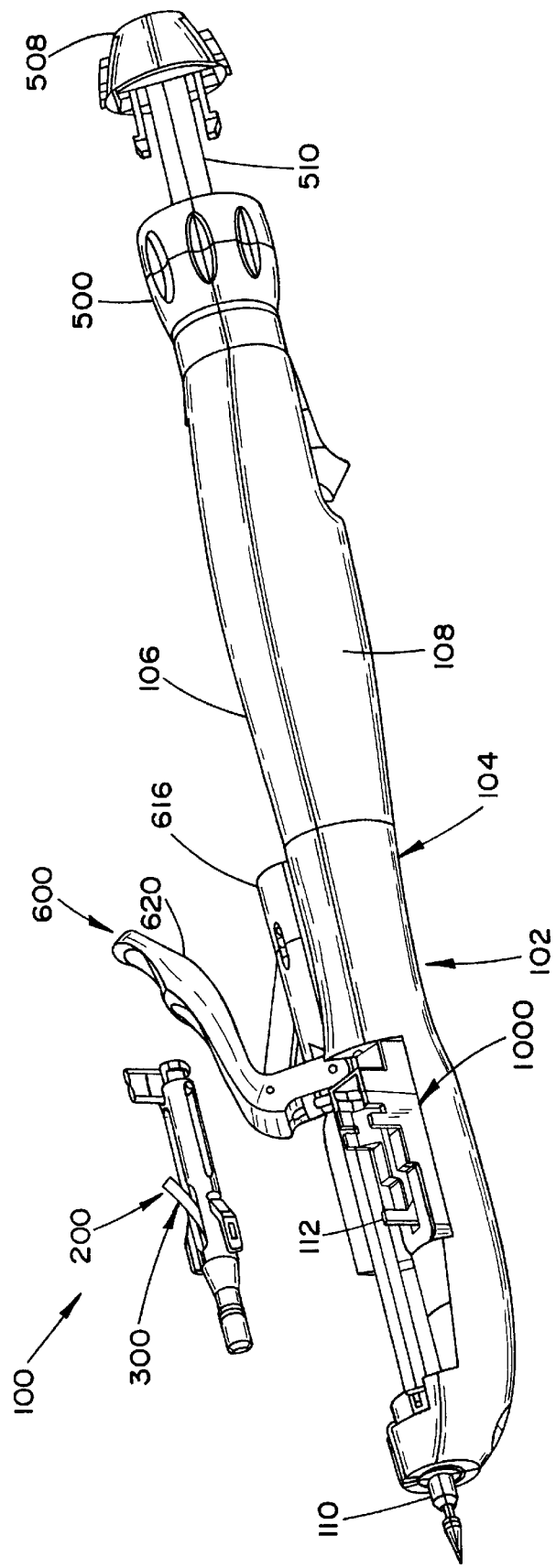
FIG. 1 illustrates a perspective view of a preferred implementation of the surgical device of the present invention.

Referring now to FIG. 1, there is illustrated a surgical device for creating an anastomosis between first and second hollow organs, the device generally referred to by reference numeral 100. As discussed above, the device is particularly useful in a CABG where the first hollow organ is the aorta and the second hollow organ is a harvested saphenous vein or radial artery or a synthetic vein. The device comprises a housing 102. The housing 100 preferably is integrated with a handle 104 for a user to grasp and manipulate the device 100. The handle is preferably fabricated from right and left halves 106, 108, respectively, which are assembled into a unitary housing for ease of assembly of internal elements. The housing 102 is fabricated from any medical grade material, preferably a thermoplastic. The housing 102 and the entire device 100 is preferably configured for an "open" type surgical procedure as shown, but may also be configured for endoscopic type procedures. Furthermore, the device 100 and/or any portions thereof can be disposable, reusable, or semi-reusable.

Figure 2:
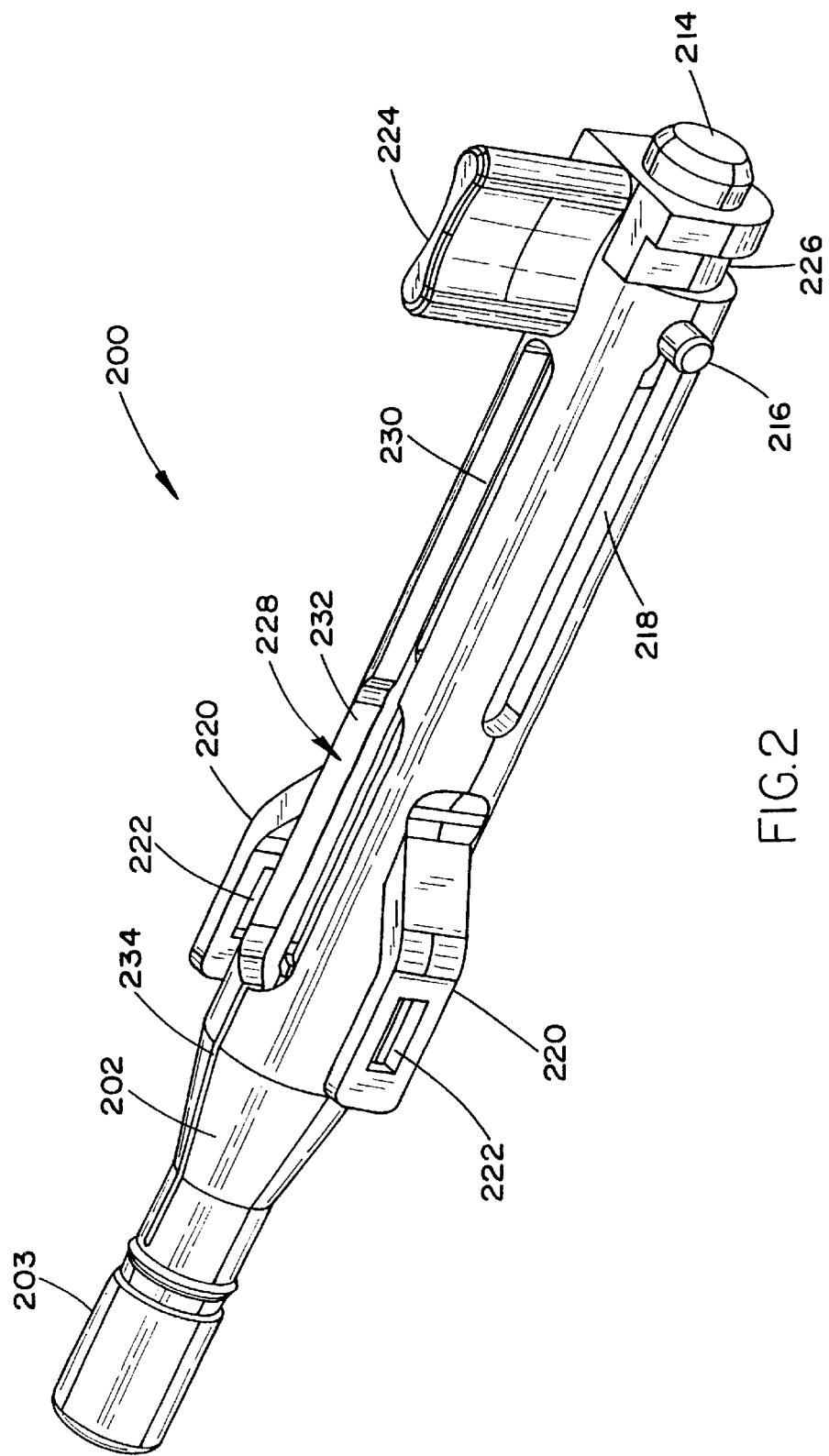
FIG. 2 illustrates a perspective view of a vessel cartridge used in the device of FIG. 1, the cartridge shown before loading of a second hollow organ therein.
Figure 3A:
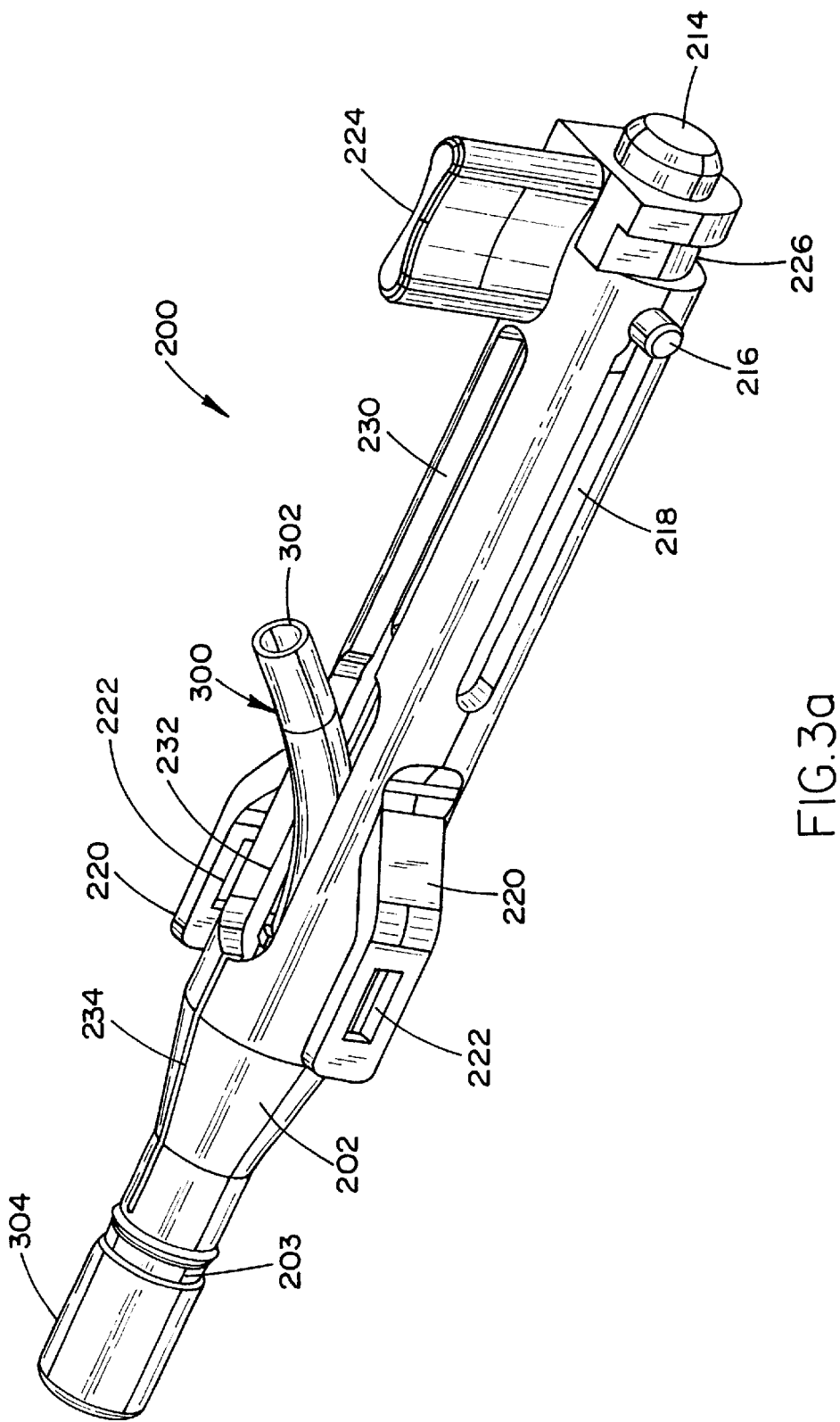
FIG. 3a illustrates a perspective view of the vessel cartridge of FIG. 2 with the second hollow organ loaded therein.
Figure 3B:
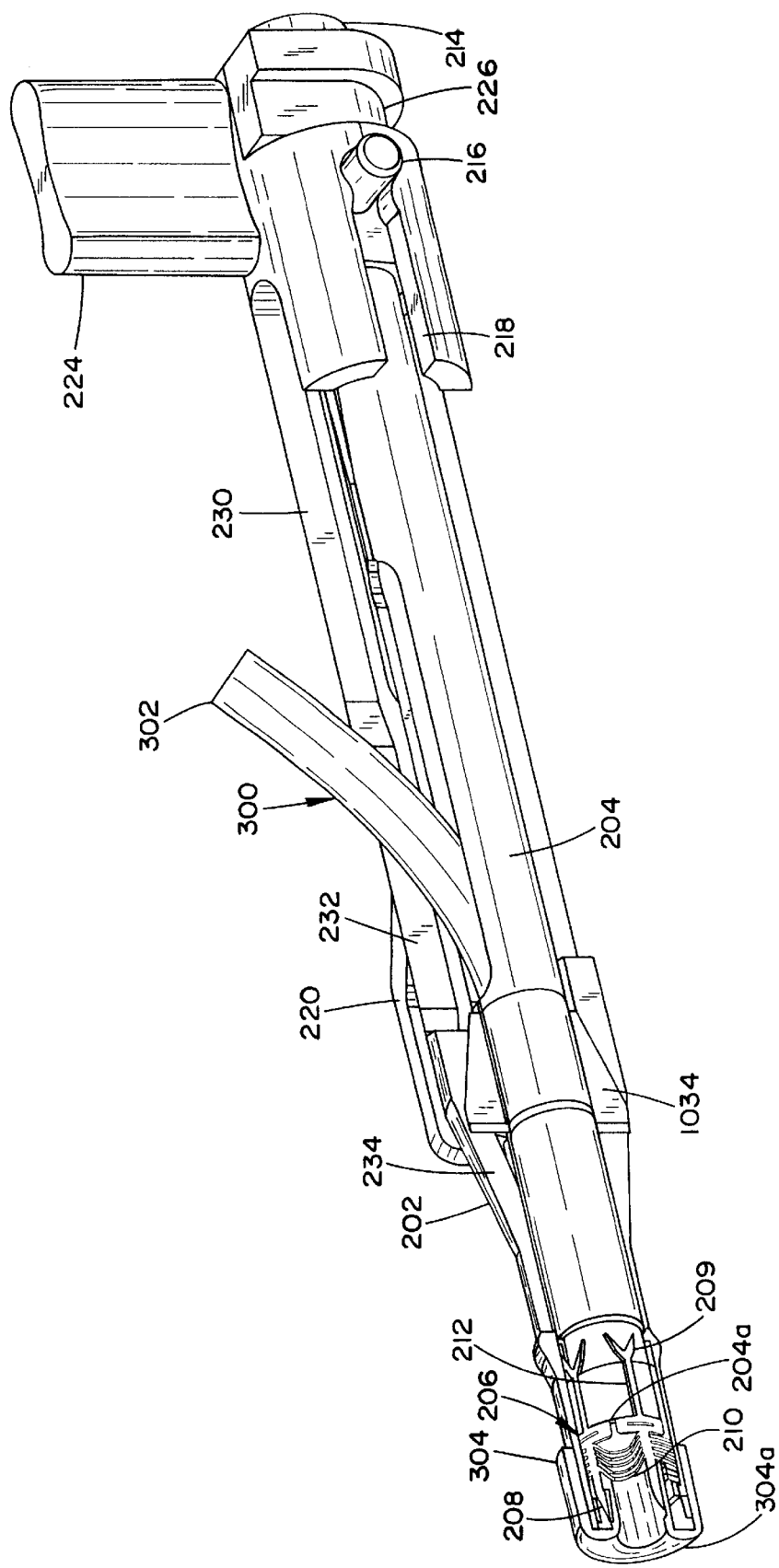
FIG. 3b illustrates a cross sectional view of the vessel cartridge of FIG. 3a with the vessel loaded therein.
Figure 3C:
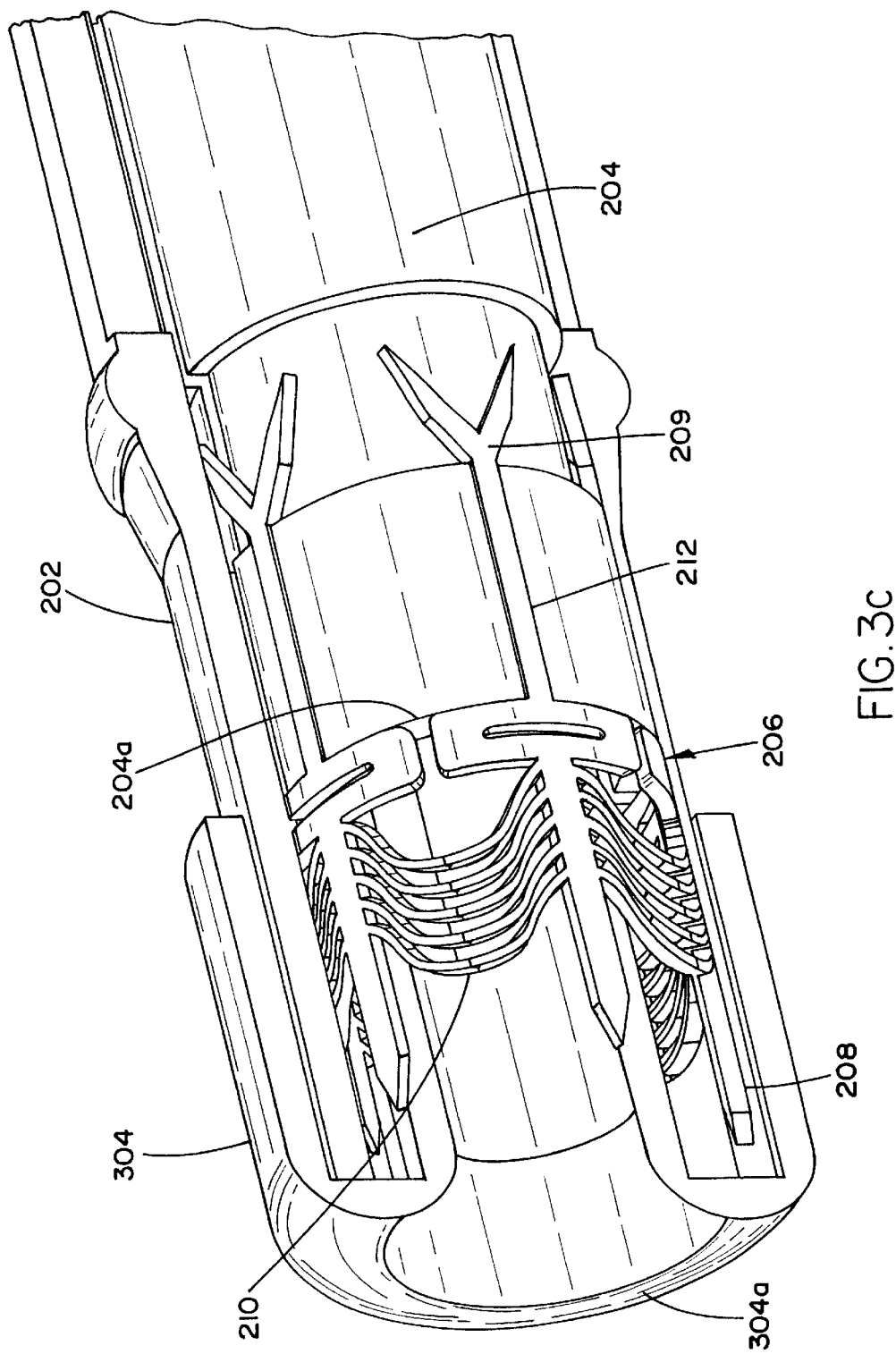
FIG. 3c illustrates a distal end of the vessel cartridge of FIG. 3b.

Referring now to FIGS. 2, 3a, and 3c, the device 100 includes a removable cartridge 200. The cartridge 200 has a body 202 having a nose section 203. The main body 202 is preferably a medical grade thermoplastic, which as discussed below can be easily split. The cartridge further has an internal contra tube 204 (alternatively referred to herein as a contra) which is preferably fabricated from a resilient medical grade material, such as stainless steel. A coupler 206 is loaded on the contra 204. The coupler 206 is preferably an anastomodic coupler which has distal and proximal sets of pins 208, 209, respectively, on the distal and proximal ends of the coupler 206. Although the proximal set of pins 209 are known as adventitia pins in the art because they deploy on the adventitial (outside) side of the aorta, they are generally referred to herein as the proximal set of pins 209. Similarly, although the distal set of pins 208 are known as intimal pins in the art because they deploy on the intimal (inside) side of the aorta, they are generally referred to herein as the distal set of pins 208. Although the distal and proximal sets of pins 208, 209 can be similarly configured, it is preferred that the proximal set include a "crows feet" configuration at their ends. The pins are normally biased in a bent position for securing the second hollow organ to a hole in the first hollow organ. The anastomodic coupler 206 further preferably has a body 210, which expands radially when deployed. Such anastomodic couplers 206 are known in the art, such as those disclosed in WO 0056228, to Loshakove et al., filed Mar. 20, 2000, which is incorporated herein by its reference. The cartridge 200 further having retaining means for retaining the pins 208, 209 in a substantially straight position and the body 210 in a contracted radial position prior to deployment of the second hollow organ and coupler 206. The retaining means generally comprises retaining the coupler 206 with the interior of the main body 202. The coupler body 210 and distal set of pins 208 are preferably disposed distally to a distal end 204a of the contra 204, and the contra 204 preferably has longitudinal grooves 212 at the distal end 204a corresponding to the proximal set of pins 209 for accepting and retaining the same therein. The contra 204 is slidingly disposed in cartridge 200 and is attached at a proximal end 204b to a button 214. The distal end 204a of the contra 204 is split while the proximal end 204b is not split. The contra also has a pin 216, which rides in a slot 218 in the cartridge body 202. The pin 216 extends past an outside surface of the cartridge body 202. Preferably, a pin 216 and slot 218 are provided on each of two sides of the cartridge 200. The cartridge body 202 further has wings 220 each having a slot 222, a handle 224, and a proximal groove 226. A slot 228 extends longitudinally on the upper side of the cartridge body 202 and having first, second, and third portions 230, 232, 234, respectively.

Referring now to FIG. 3a, the cartridge 200 is illustrated therein after loading with the second hollow organ 300, which is generally a harvested vein. The second hollow organ 300 is passed through a lumen in the cartridge 100 with its proximal end 302 exiting through the second portion 232 of the slot 228 and its distal end 304 being everted over the nose section 203 of the cartridge body 202. Typically, the second hollow organ 300 such as a harvested vein to be used in a CABG procedure is approximately 10 inches long, in which case the proximal end 302 hangs free from the cartridge 200. However, the proximal end 302 of the second hollow organ 300 is shown shortened for clarity.

Figure 4A:
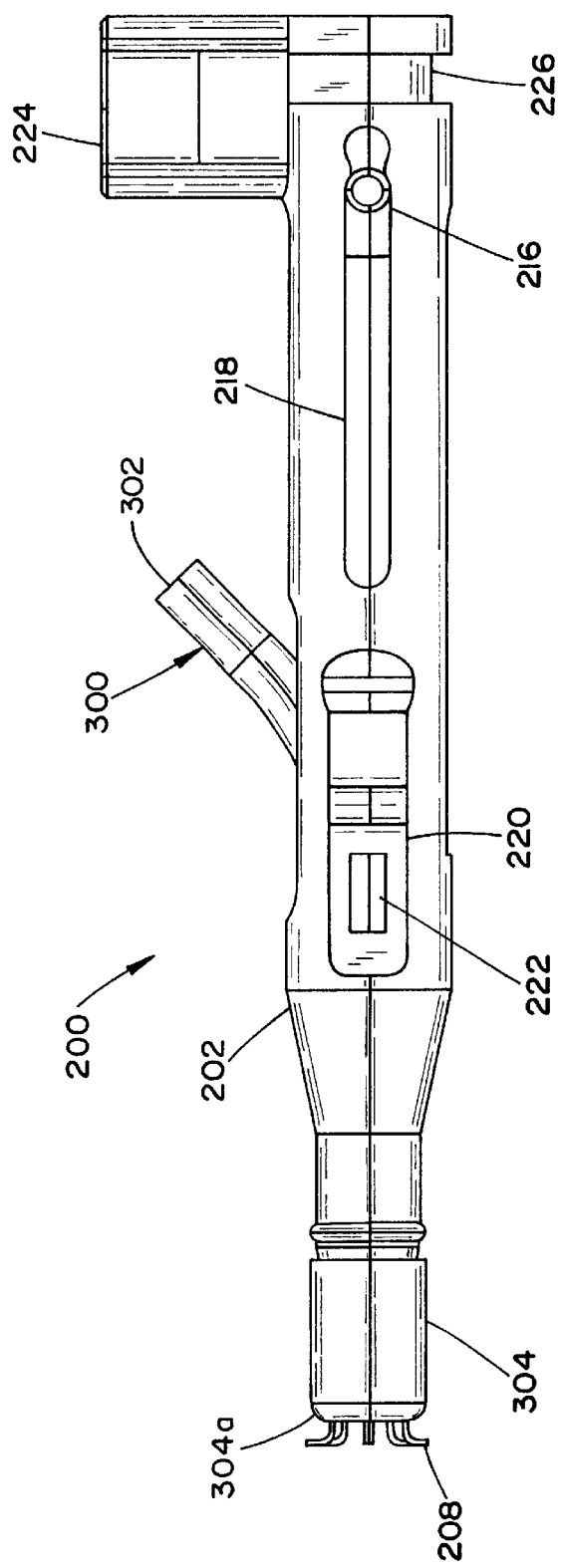
FIG. 4a illustrates a side view of the cartridge of FIGS. 2 and 3 with the pins of a coupler device pierced through an everted portion of the loaded second hollow organ.
Figure 4B:
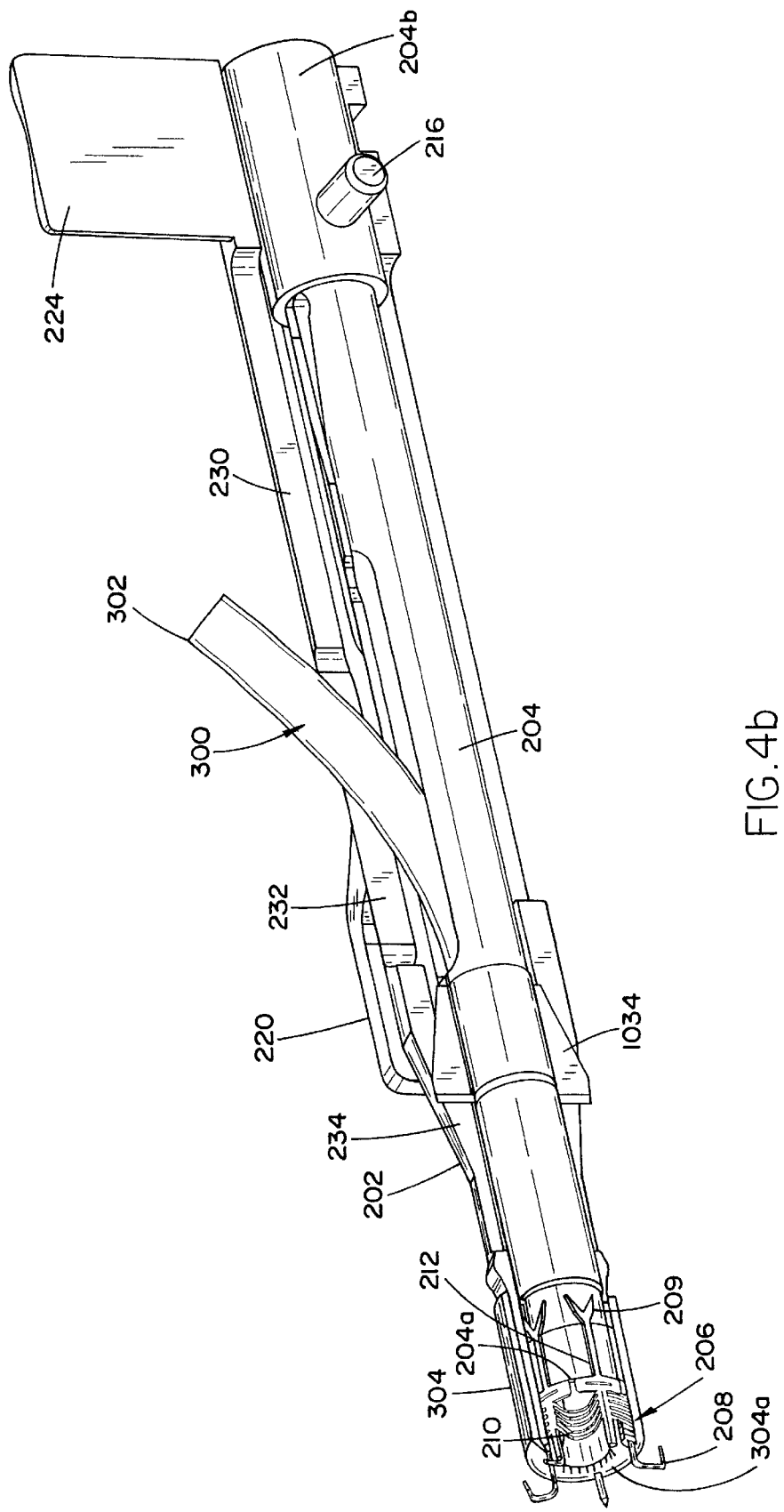
Figure 4C:
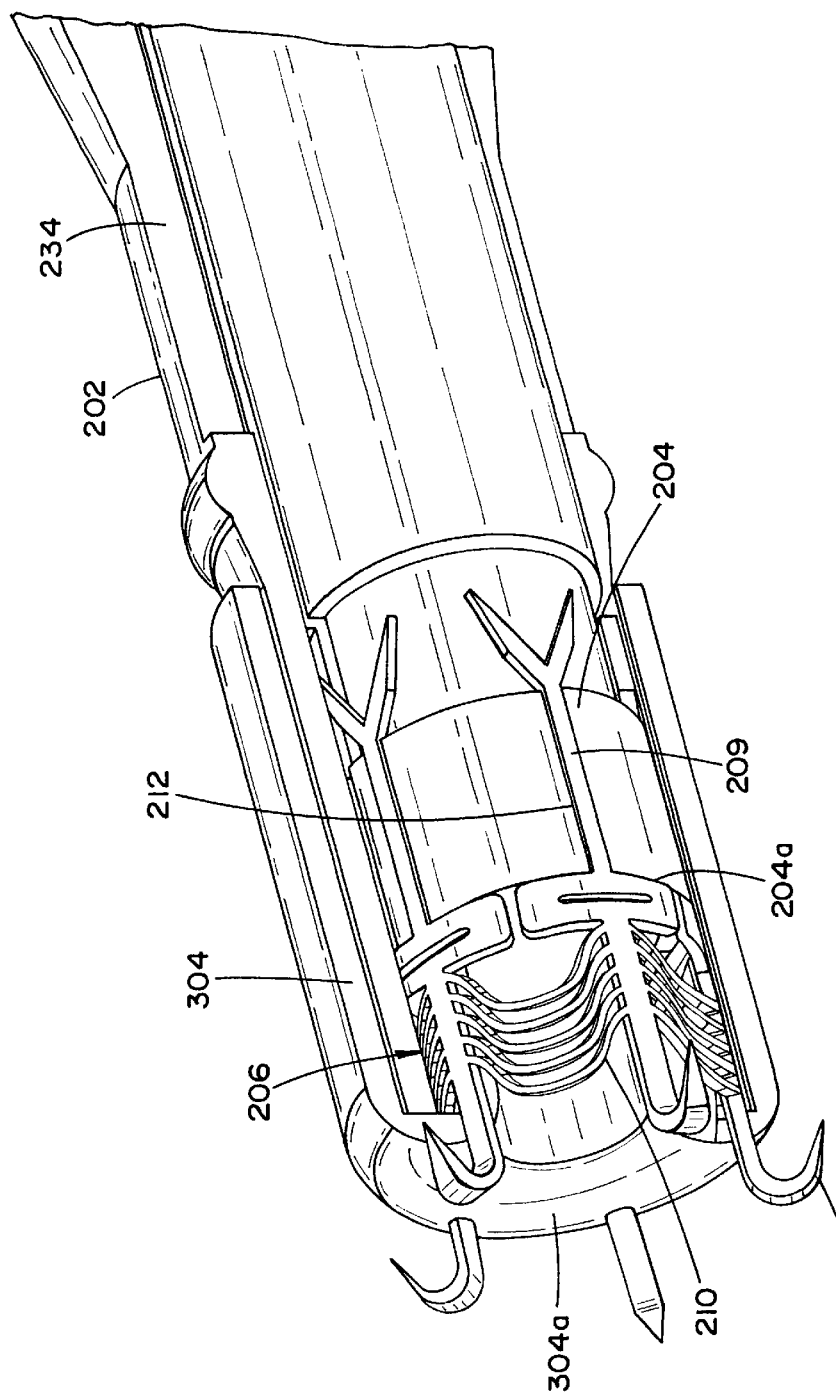
FIG. 4c illustrates a distal end of the vessel cartridge of FIG. 4b.

Referring now to FIG. 4, prior to loading the cartridge 200 in the device 100, the button 214 is depressed distally into the cartridge body 202 to slide the contra 204 distally relative to the cartridge body 202 which causes the pins 216 to move distally in their corresponding slot 218 and which further moves the coupler 206 distally until some of the restraint on the distal set of pins 208 is removed whereby the distal set of pins 208 pierce the folded portion 304a of the everted distal end 304 of the second hollow organ 300 and partially return to their bent position. Therefore, before loading the cartridge 200 into the housing 102, the second hollow organ can be inspected to determine if it is adequately pierced by the distal set of pins 208.

Figure 5A:
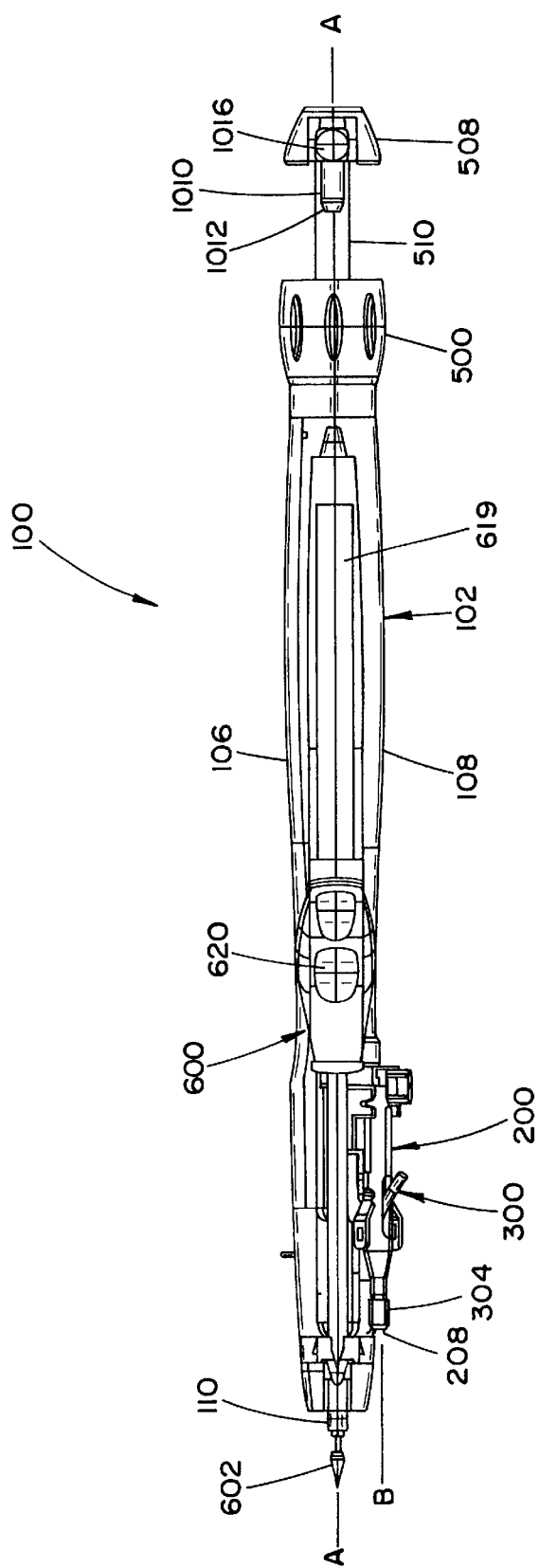
FIG. 5a illustrates a top view of the surgical device of FIG. 1 with the cartridge loaded therein and the punch in the cutting position.

Referring now to FIG. 5a, the cartridge 200 is then disposed in the housing 102, preferably in a distal portion of the housing 102. The cartridge 200 is movably disposed in the housing between a cutting position and a deploying position. The cutting position is defined as any position in which the cartridge 200 does not interfere with the cutting of a hole in the first hollow organ and in which a punch assembly 600 is positioned to make the hole in the first hollow organ. The deploying position is defined as any position in which the cartridge 200 is positioned to deploy the second hollow organ 300 into the hole in the first hollow organ and in which the punch assembly 600 is positioned so as not to interfere with the cartridge 200. FIG. 5a shows the punch assembly 600 and cartridge in the cutting position. A punch tip 602 of the punch assembly 600 is extended about a central axis A and the cartridge is offset from the central axis A about axis B.

The cartridge 200 is preferably rotated between the cutting and deploying positions, as will be discussed below. However, the cartridge 200 can also translate between the cutting and deploying positions. Furthermore, the cartridge 200 is preferably rotated from an axis B which is offset from axis A, as will also be discussed below. However, the cartridge 200 and the distal end of the punch assembly 600 do not have to be on offset axes. For instance, although not preferred, the cartridge 200 can translate along the central axis A between cutting and deploying positions where the punch assembly 600 is flexible and slides around the cartridge 200 while in the cutting position where the distal end of the punch assembly 600 slides along central axis A and the remainder slides along an offset axis.

Figure 5B:
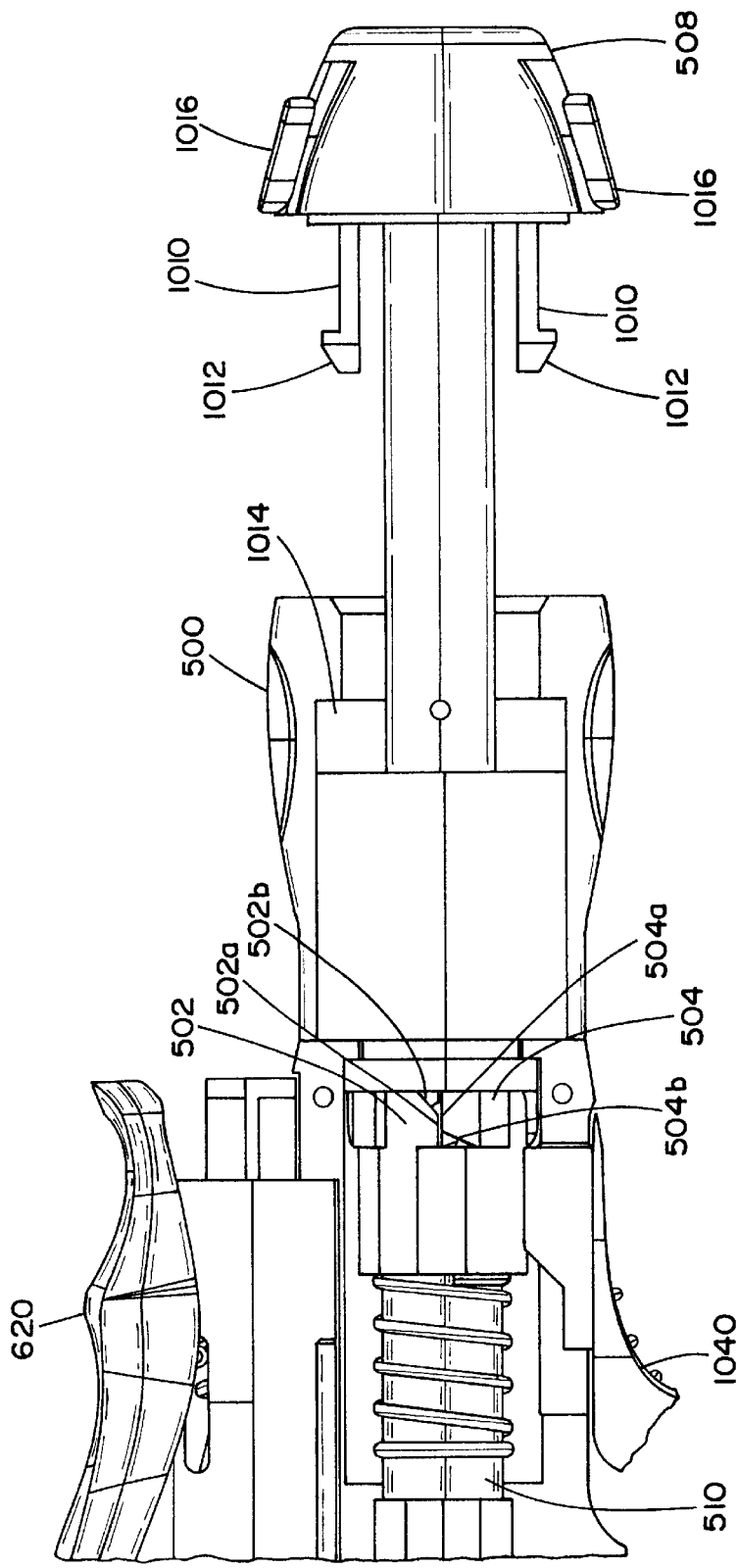

Referring now to FIG. 5b, a cross sectional view of the proximal end of the housing 202 is shown corresponding to the device 100 illustrated in FIG. 5a, that is, where the cartridge 200 is in the cutting position and the punch assembly 200 is proximally retracted from the cutting position but free to be deployed into the cutting position. While initially in the cutting position, a knob 500, rotation of which is used to deploy the second hollow organ 300, is locked from rotation. The knob is preferably locked with gears 502, 504 one of which is attached to the knob 500 and the other of which is biased proximally by a spring 506. In the locked position, horizontal portions 502a, 504a of the gears 502, 504, respectively, are engaged which prevent relative motion of the knob 500 with respect to the screw tube 506. Furthermore, while in the initial cutting position, namely after initially loading the cartridge 200 into the housing 102, a knob cap 508 is retracted proximally from the housing 102. The knob cap is connected to a proximal end of a screw tube 510, which engages the cartridge 200 at a distal end.

Figure 6:
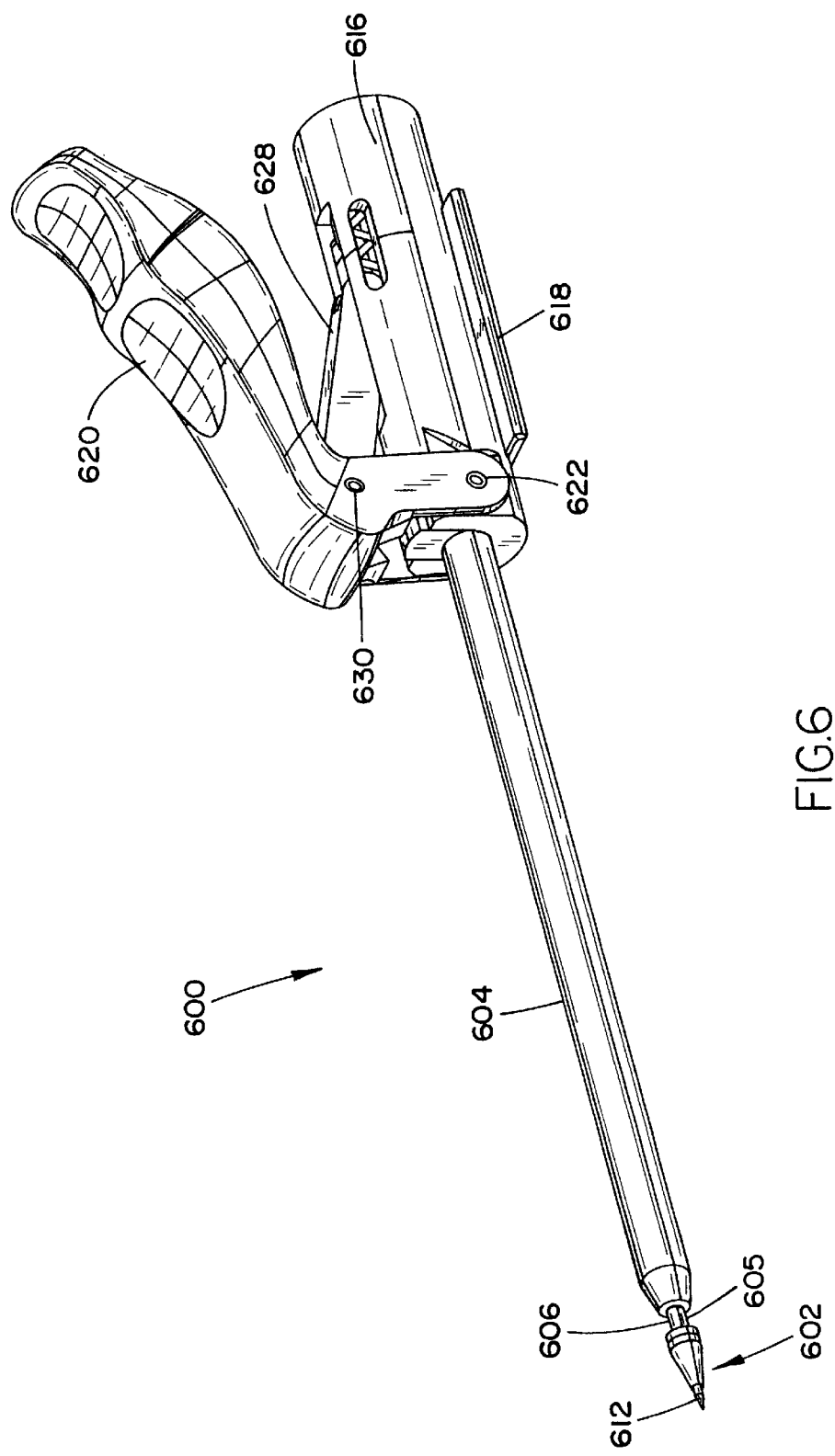
FIG. 6 illustrates an isometric view of the punch assembly of the surgical device of FIG. 5.
Figure 7A:
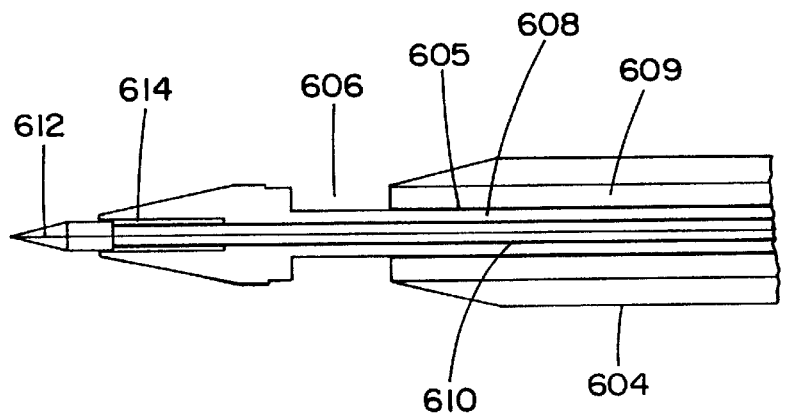
FIG. 7a illustrates a cross sectional view of a distal portion of the punch assembly of FIG. 6 with the punch point extended.
Figure 7B:
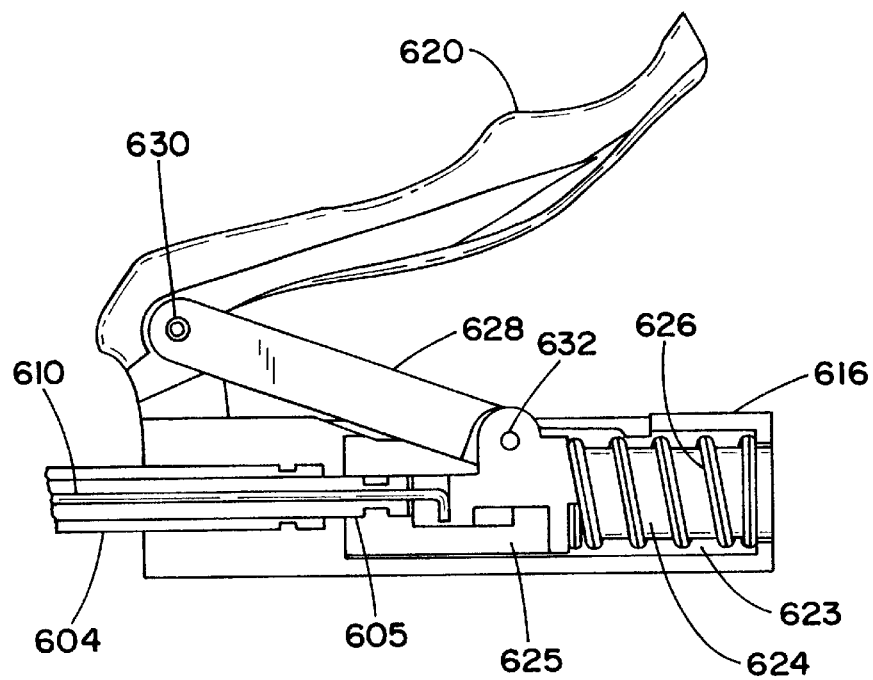
FIG. 7b illustrates a cross sectional view of a proximal portion of the punch assembly of FIG. 6 with the handle positioned to correspond to the punch point being extended.
Figure 12:
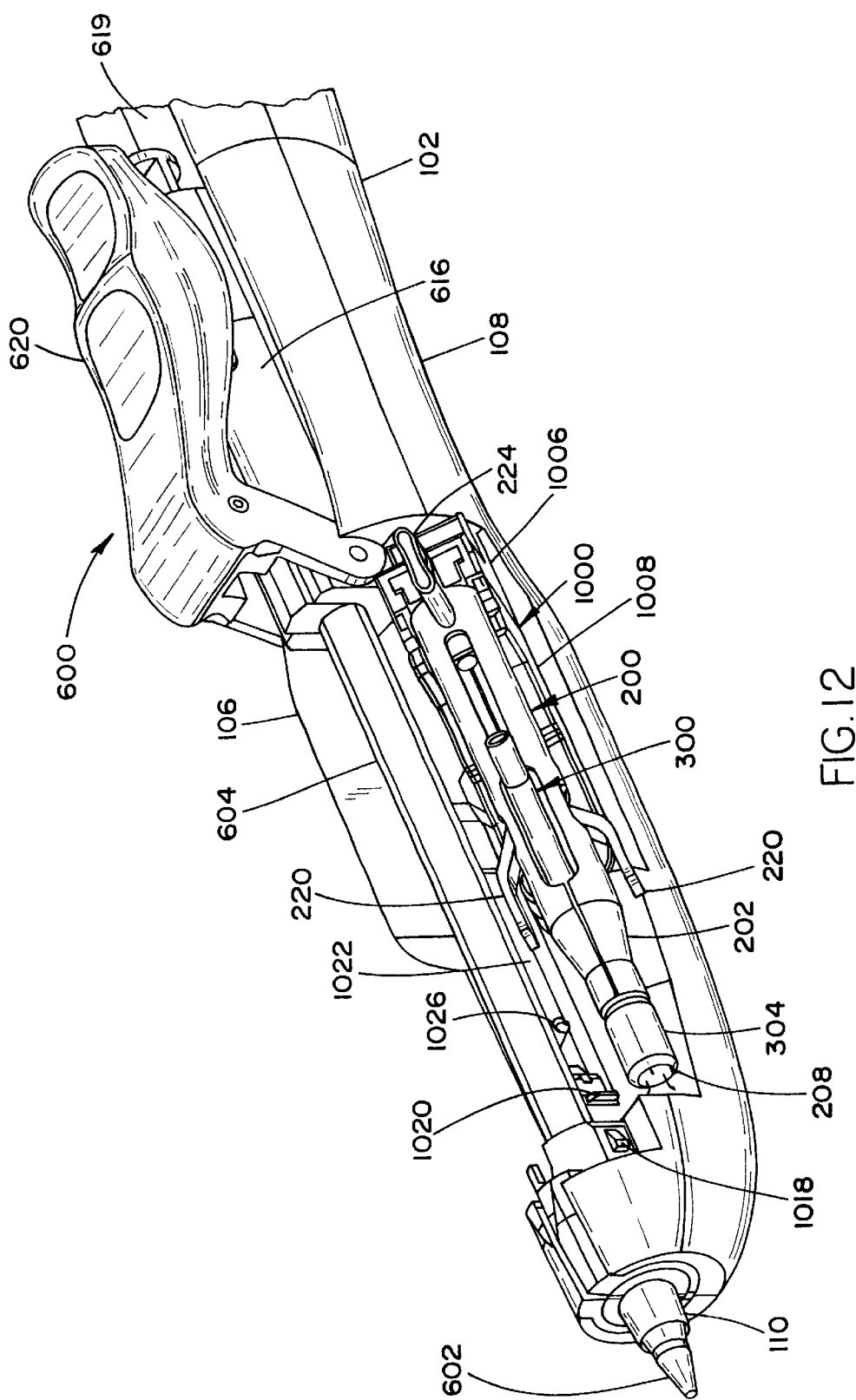
FIG. 12 illustrates an isometric view of a distal portion of the surgical device of FIG. 5 with the punch tip retracted to cut a hole in the first hollow organ.

Referring now to FIGS. 6, 7a, and 7b there is illustrated a punch assembly 600, alternately referred to simply as a punch 600 for forming a hole in the first hollow organ. The punch 600 is preferably slidingly disposed in the housing 102. The punch 600 has an outer punch tube 604 fixed at a proximal end to a punch body 616 and having a lumen 609. The punch 600 further has an inner punch tube 605 disposed in the lumen 609 and has a grooved portion 606 and punch tip 602 at a distal end. The inner punch tube 605 has a lumen 608 for acceptance of a punch shaft 610. The punch shaft 610 has a punch point 612, which retracts into a distal portion 614 of the lumen 608. The punch body also has a punch slide 618 for engaging a corresponding slot 619 (shown in FIG. 12) in the housing 102 to retain and slidingly dispose the punch 600 therein.

The punch body 616 further has a punch lever 620 rotatably disposed thereon about a first pined joint 622. The punch body 618 further has an internal cavity 623 in which a plunger 624 is slidingly disposed. The plunger is biased toward the distal direction by a spring 626. The punch shaft 610 is connected to the plunger 624 while the inner punch tube 605 is connected to a slide 625, which is also slidingly disposed in the internal cavity 623. The punch lever 620 is further connected to the plunger 624 by a link 628 having a rotatably pinned connection at each of two ends 630, 632. While the punch lever 620 is in an upright position as shown in FIGS. 1, 6, and 7b, the punch point 612 is extended from the punch tip 602 to facilitate piercing of a wall of the first hollow organ, such as the aorta.

Figure 8:
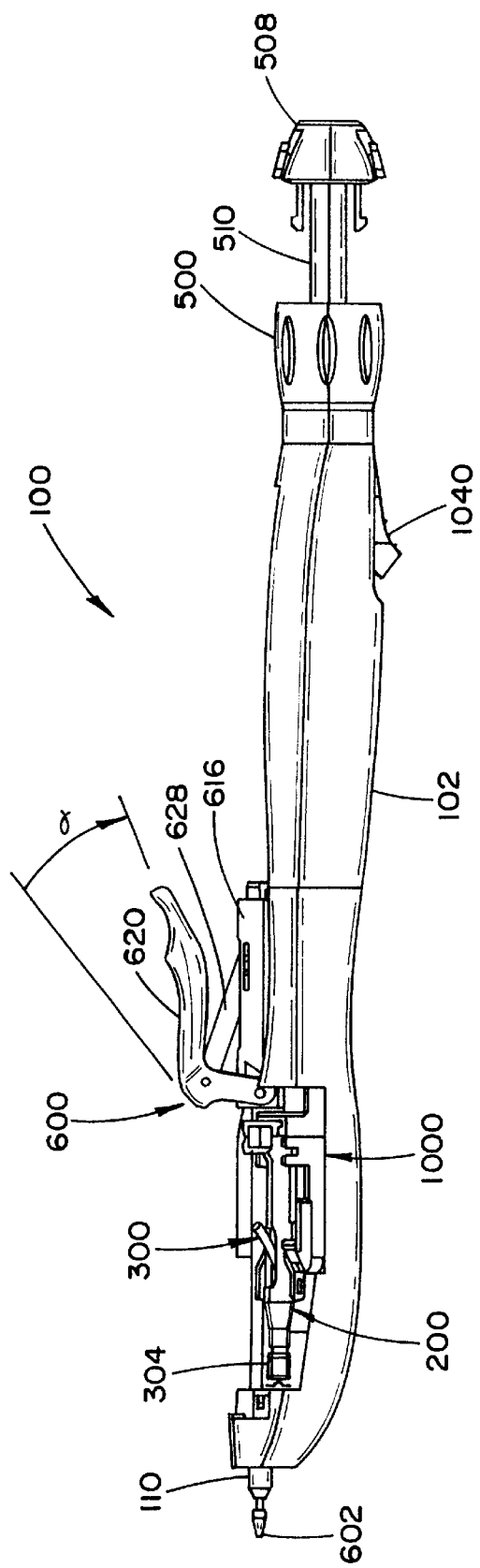
FIG. 8 illustrates a side view of the surgical device of FIG. 5 with the punch point retracted.
Figure 9A:
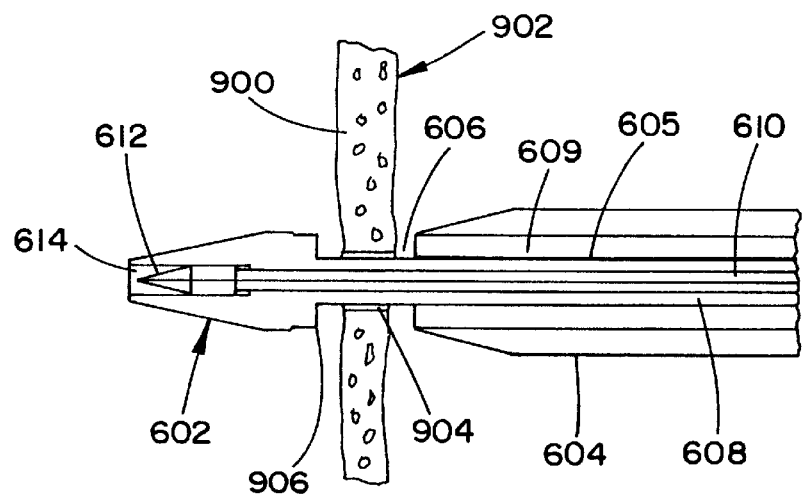
FIG. 9a illustrates a cross sectional view of a distal portion of the punch assembly of FIG. 6 with the punch point retracted.
Figure 9B:
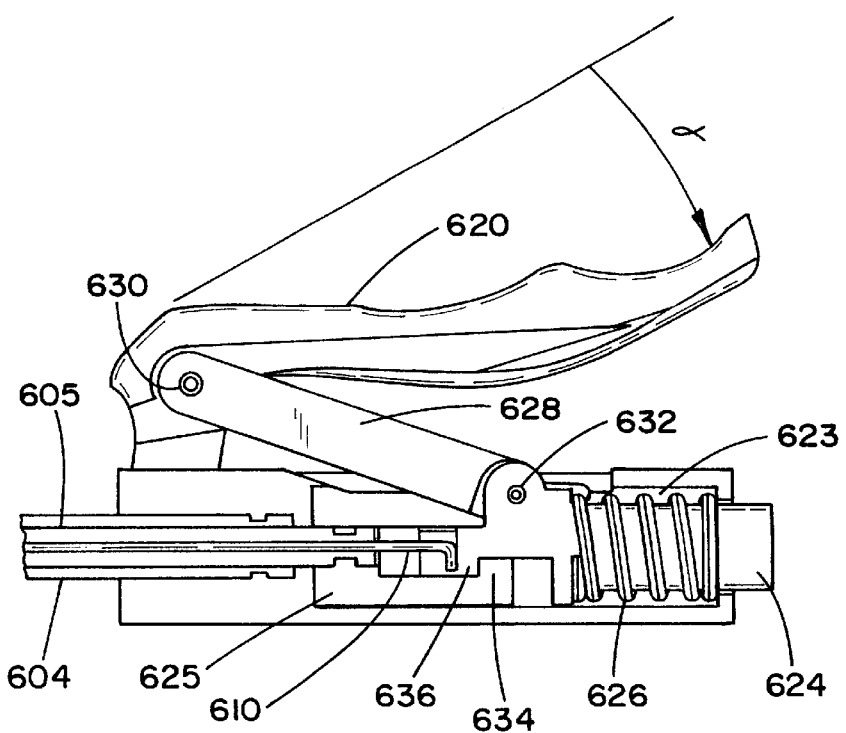
FIG. 9b illustrates a cross sectional view of a proximal portion of the punch assembly of FIG. 6 with the handle positioned to correspond to the punch point being retracted.
Figure 10:
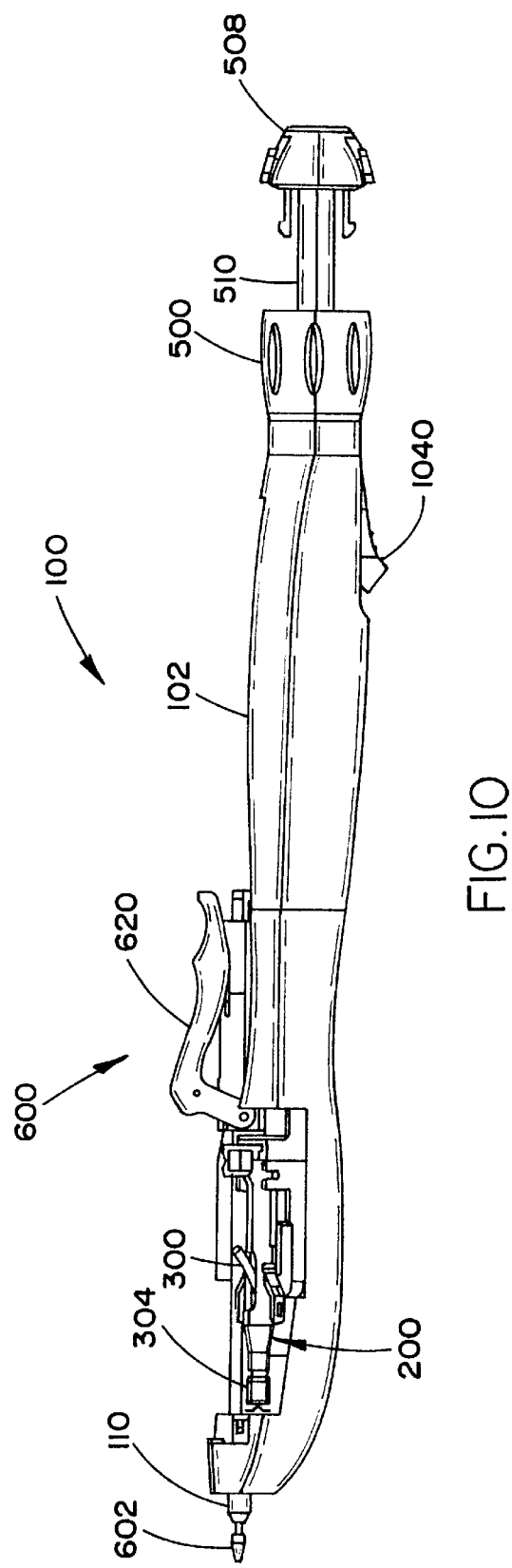
FIG. 10 illustrates a side view of the surgical device of FIG. 5 with the punch tip retracted.

Referring now to FIGS. 8, 9a, and 9b, after piercing the wall 900 of the first hollow organ 902, the punch point 612 is retracted, as shown in FIGS. 8 and 9b, by rotating the punch lever 620 a first predetermined angle α from the position shown in FIG. 7b. Rotating the lever 620 causes the link 628 to slide the plunger 624 proximally against the bias of the spring 626 which pulls the punch shaft 610 proximally until the punch point 612 retracts into the distal portion 614 of the lumen 608 and a stop 634 on the slide 625 engages a corresponding stop 636 on the plunger 624. Preferably, the punch point 612 is retracted immediately after piercing the wall so as to minimize the possibility of piercing completely through (backwalling) the first hollow vessel. As shown in FIG. 9a, after piercing the wall 900 of the first hollow organ 902, a puncture 904 is created in the wall 900 and with further pressure in the distal direction, the wall 900 is positioned in the grooved portion 606 of the punch tube 604.

Figure 11A:
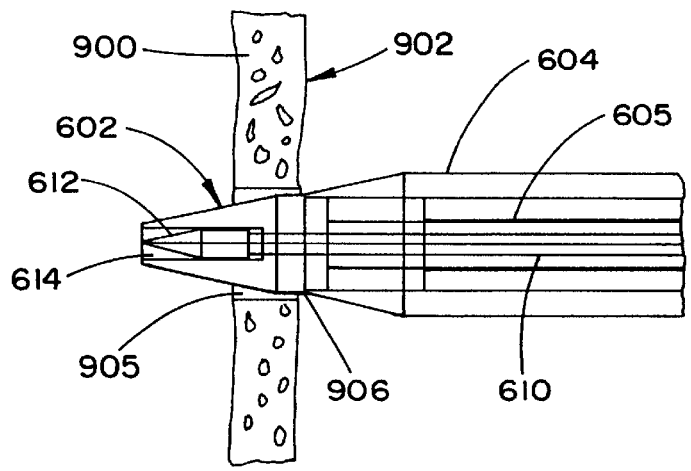
FIG. 11a illustrates a cross sectional view of a distal portion of the punch assembly of FIG. 6 with the punch tip retracted.
Figure 11B:
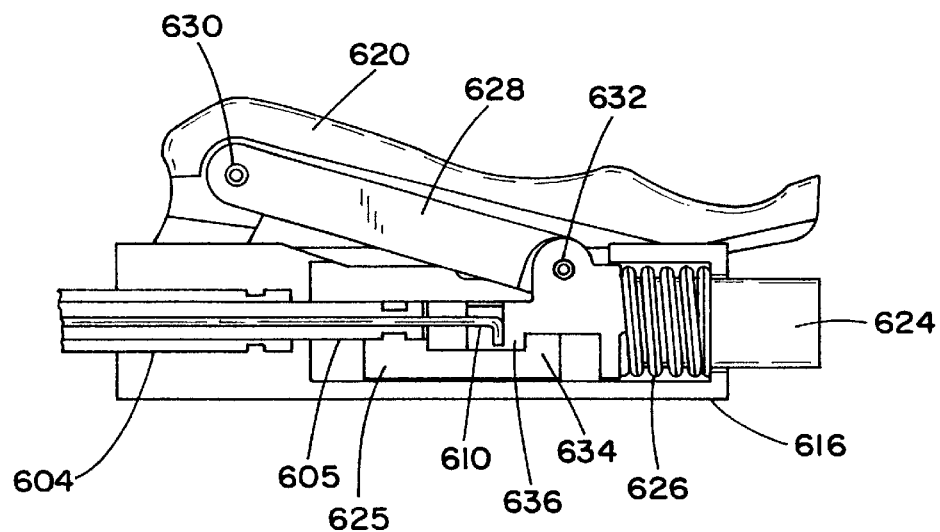
FIG. 11b illustrates a cross sectional view of a proximal portion of the punch assembly of FIG. 6 with the handle positioned to correspond to the punch tip being retracted.

Referring now to FIGS. 10, 11a, 11b, and 12, the captured wall 900 in the grooved portion 606 is cut to form a hole 905 for subsequent insertion of the second hollow organ 300. To cut the hole 905, the punch tip 602 is retracted by depressing the lever 620 completely as shown in FIG. 11b to withdraw the inner punch tube 605 against the outer punch tube 604. Upon depressing the lever 620 past the angle α, the stops 634, 636 are engaged and the plunger 624 drags the slide 625 proximally to retract the inner punch tube 605. The cutting of the hole is accomplished with a rear cutting edge 906 of the punch tip 602 that presses against a corresponding surface for the outer punch tube 604 to cut the hole 905. After cutting the hole 905, a nose sleeve 110 disposed on the distal portion of the housing 102, and approximately the same size as the hole 905, is positioned into the hole 905.

Figure 13:
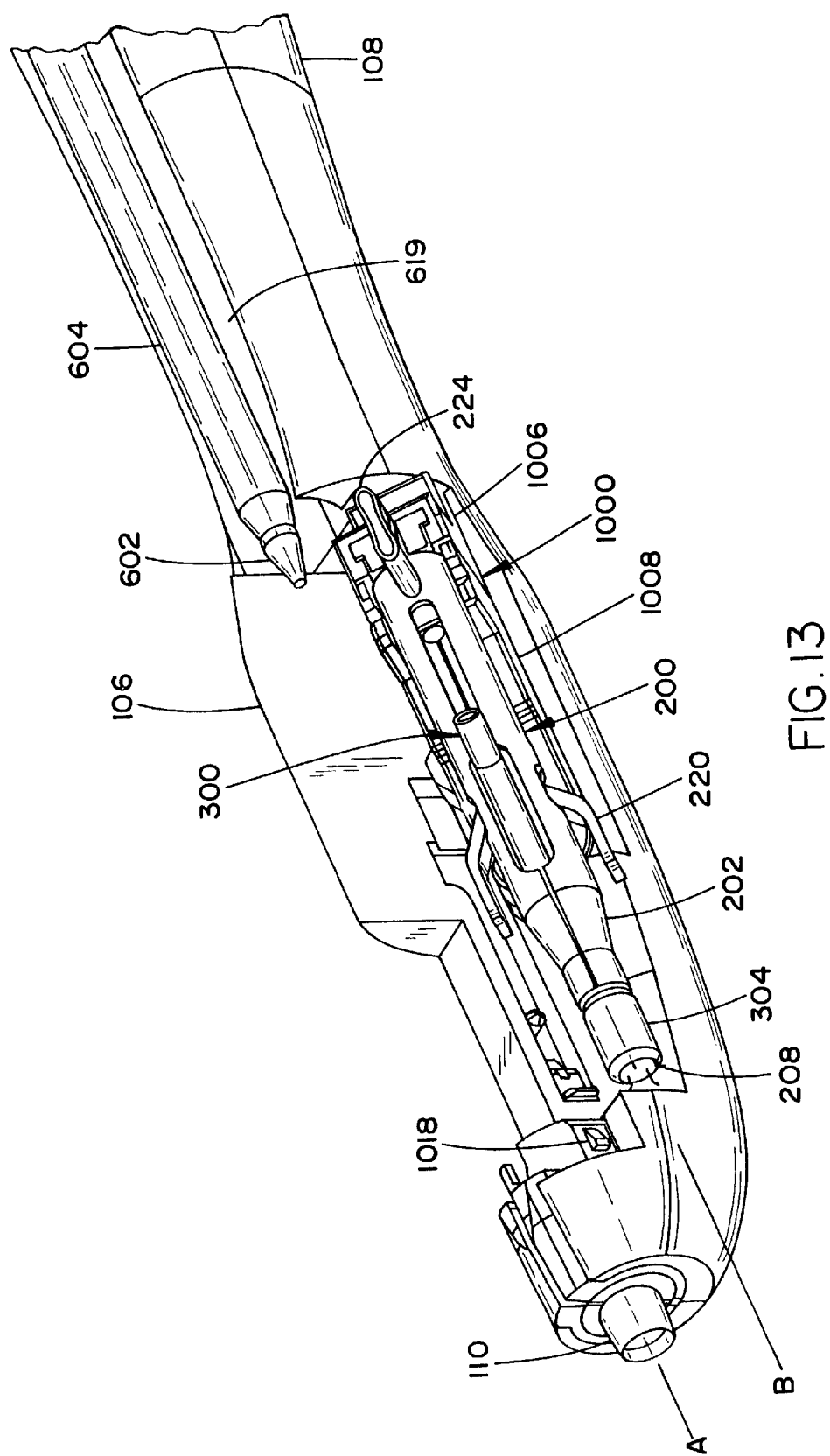
FIG. 13 illustrates an isometric view of a distal portion of the surgical device of FIG. 12 with the punch assembly retracted into a deploying position.
Figure 14A:
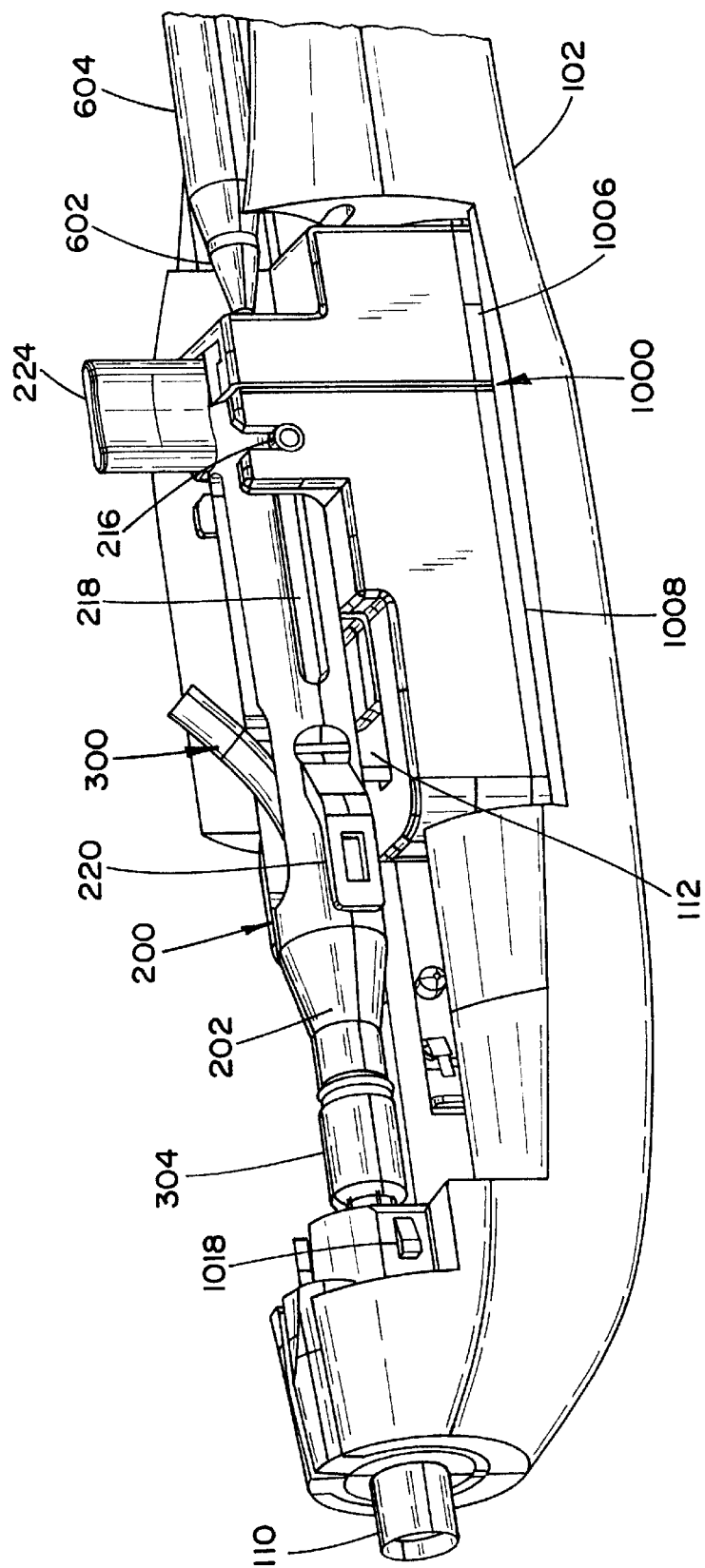
FIGS. 14a and 14b illustrate isometric views of the surgical instrument of FIG. 13 with the cartridge rotated into the deploying position.
Figure 14B:
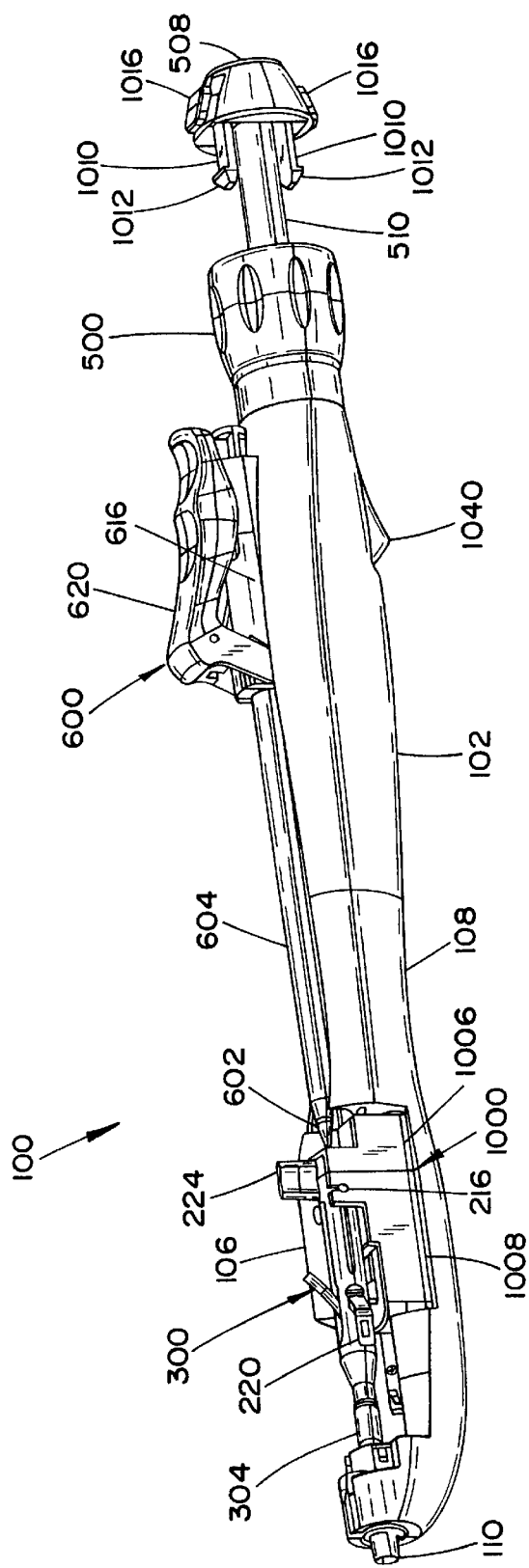

Referring now to FIGS. 13, 14a, and 14b, with the nose sleeve 110 inserted into the hole 905, a punch actuation means is used to slide the punch 600 between the cutting and deploying positions. Preferably, as discussed above, the punch slide 618 of the punch body 616 slides in the slot 619 of the housing 102 to move the punch 600 proximally from the cutting position into the deploying position. Preferably, the punch 600 includes a means for locking the punch lever 620 and punch 600 in the deploying position. After retraction of the punch 600, a seal 633 (shown in FIG. 18) in the distal portion of the housing prevents any liquid in the first hollow organ from entering the device. The seal 633 is preferably an elastomer sheet with a tiny puncture, which stretches for passage of the punch tip 602 and cartridge 200 and which returns to its shape after withdrawal of the punch 600. Once the punch 600 is in the deploying position, a cartridge actuation means is used to move the cartridge from the cutting position to the deploying position. As shown in FIG. 14a, and discussed above, the cartridge 200 is preferably rotated into the deploying position. FIG. 14b shows the punch 600 retracted proximally into the deploying position, the cartridge 200 rotated into alignment with the central axis, which is centered on the hole 905, and the knob cap 508 retracted proximally.

Figure 15A:
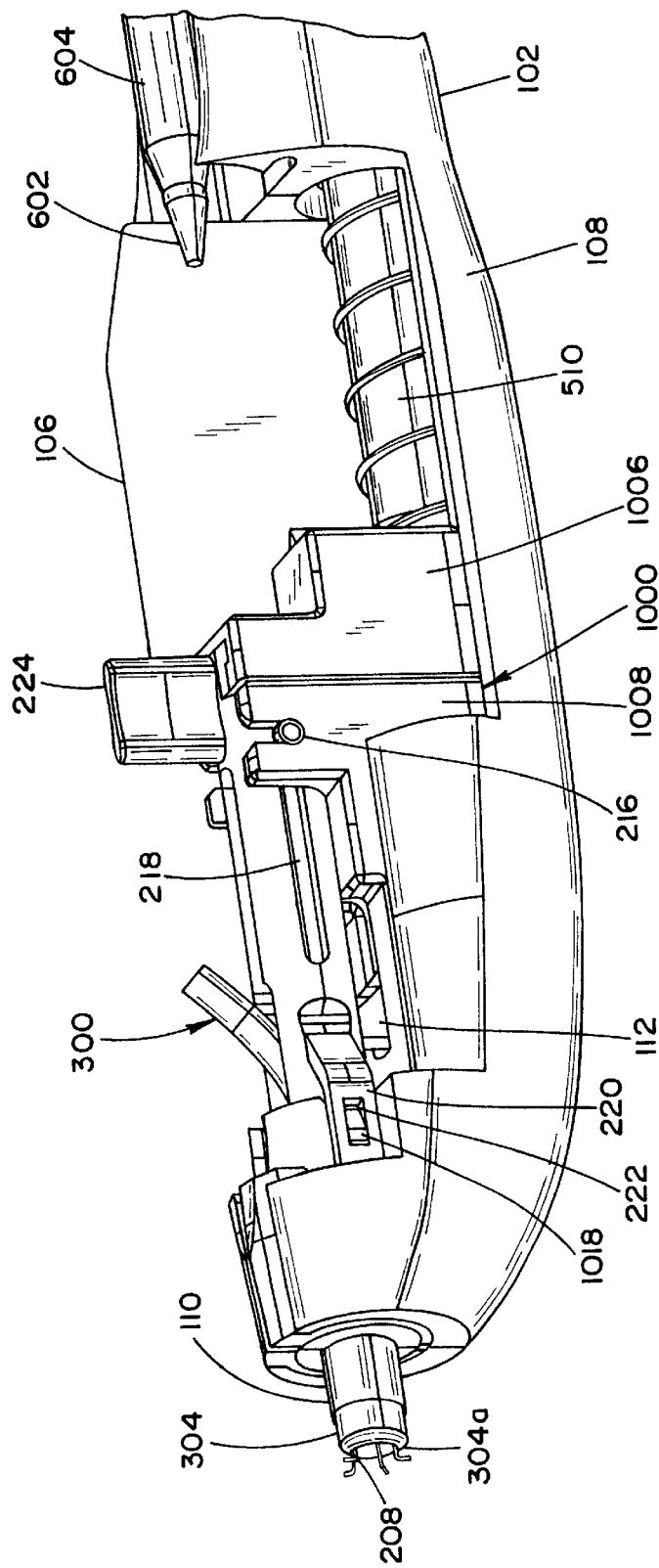
FIGS. 15a and 15b illustrate isometric views of the surgical instrument of FIGS. 14a and 14b with the cartridge indexed distally such that the everted portion of the second hollow organ protrudes from the distal portion of the surgical device.
Figure 15B:
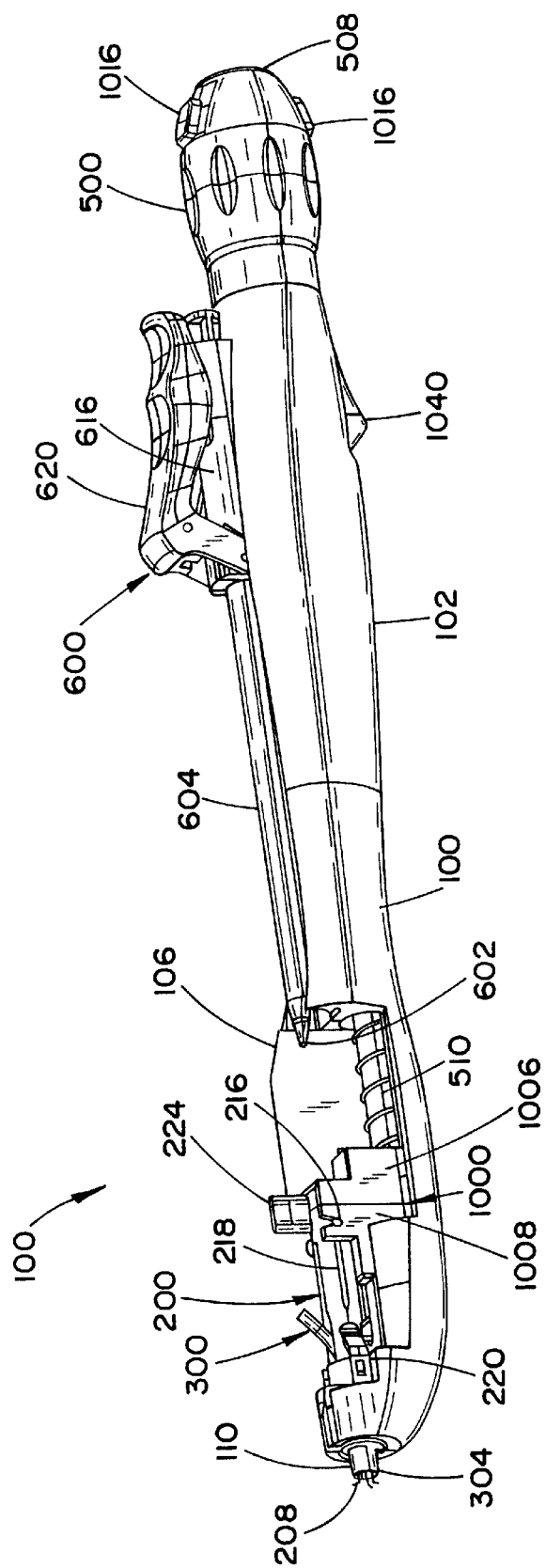
Figure 15C:
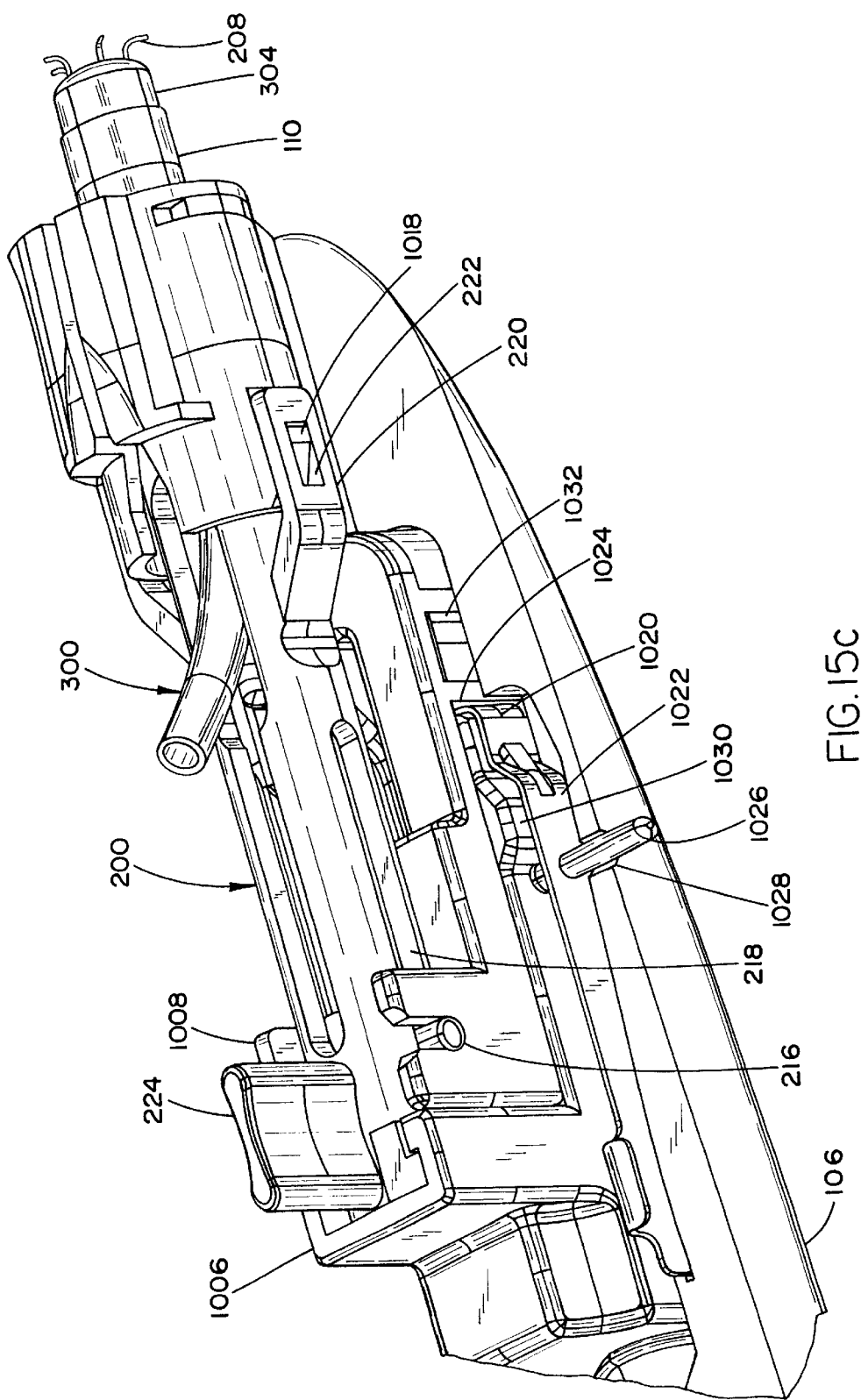
FIG. 15c illustrates an isometric view of the distal portion of the surgical instrument of FIGS. 15a and 15 showing an initial position of a timing mechanism for deploying the second hollow organ and coupler.
Figure 15D:
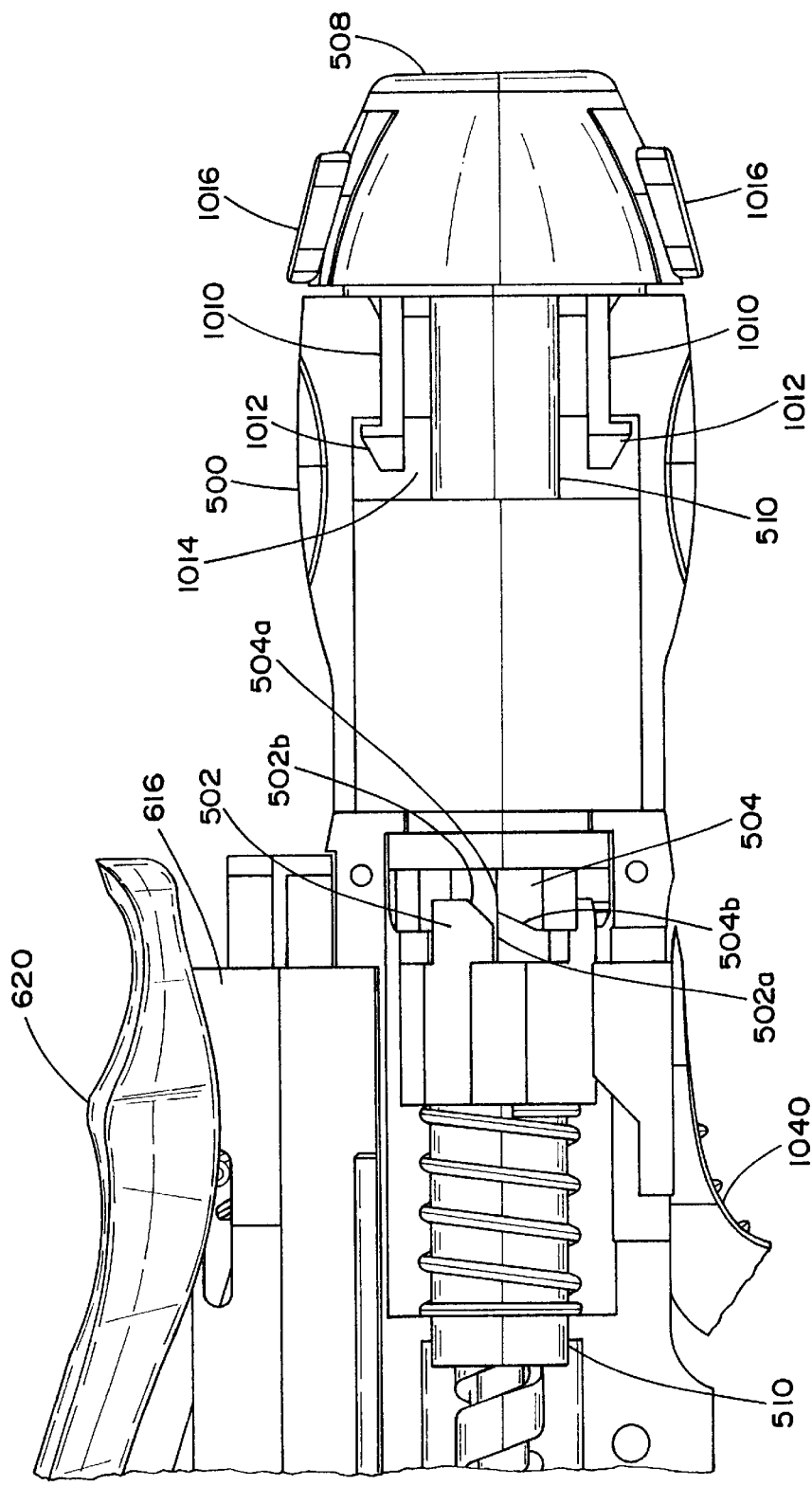
FIG. 15d illustrates a section view corresponding to the proximal end of the surgical device of FIG. 15b.
Figure 16A:
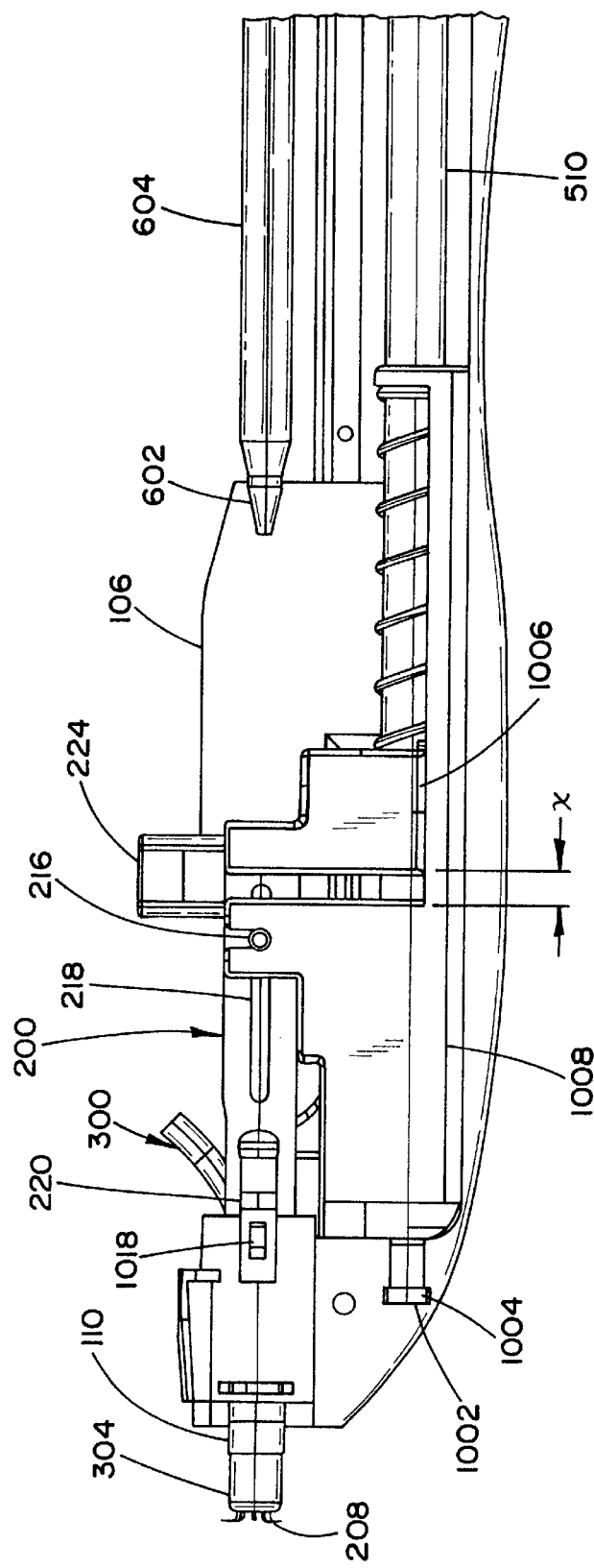
FIG. 16a illustrates a side view of a distal portion of the surgical instrument of FIGS. 15a and 15b in which the cartridge pull plate is pulled proximally.

Referring briefly to FIGS. 15a and 16a, the cartridge is loaded shown loaded onto a cradle 1000, the cradle is rotatably disposed in the housing 102 by way of a distal portion of the screw tube 510. The screw tube 510 runs through the cradle 1000 and is retained in housing 102 by a groove 1002 and corresponding tab 1004 on the screw tube 510. The cradle 1000 includes a cartridge pull plate 1006 and a contra pull plate 1008. The cartridge pull plate 1006 engages the cartridge body 202 at the slot 226 and the contra pull plate 1008 engages the contra 204 by way of the pins 216 and corresponding slots 217 on the contra pull plate 1008. The cradle 1000 further has a wedge 112, which engages a lower slot of the cartridge 200.

Referring now to FIGS. 15–18, a preferable deploying means for deploying the second hollow organ and coupler into the hole to create the anastomosis will be described. Referring first to FIGS. 15a, 15b, 15c, and 15d, subsequent to the cartridge 200 being rotated into the deploying position, the knob cap 508 is advanced distally to engage the knob 500. Preferably, the knob 500 and knob cap 508 engage by means of tabs 1010 having hook ends 1012, which are captured, in a cavity 1014 in the knob 500. Tab buttons 1016 are also provided to release the knob cap 508 from the knob 500. The advancement of the knob cap 508 advances the screw tube 510, which in turn advances the cartridge 200 and the cradle 1000 distally such that the everted portion 304 of the second hollow organ 300 protrudes through the nose 110 and into the hole 905 thereby locking the cartridge 200 in the deploying position. At this point, the distal set of pins 208 embed in an inner surface of the wall 900 circumferentially about the hole 905.

Also upon advancement of the knob cap 508, the slot 222 in the wings 220 of the cartridge body 202 engage a corresponding protrusion 1018 on the nose piece 110 of the housing 102. Further, a distal free end 1020 of a leaf spring 1022 disposed in the housing 102 engages a first slot 1024 in the contra pull plate 1008. The leaf spring 1022 further has a pin 1026 fixed to the leaf spring 1022 and slidingly disposed in a hole 1028 in the housing 102. As will be discussed later, the leaf spring is a preferred implementation of a timing means for timing the movement of the cartridge and contra pull plates 1006, 1008. Lastly, upon advancement of the knob cap 508, causes gear 502 to advance distally such that tapered portions 502b, 504b of gears 503, 504 engage upon rotation in one direction (clockwise) thereby permitting a ratchet type motion of the knob 508 and screw tube 510. In this position, the knob 500 and screw tube 510 attached thereto can rotate in the clockwise direction but are restricted from rotating in the counterclockwise direction.

Figure 16B:
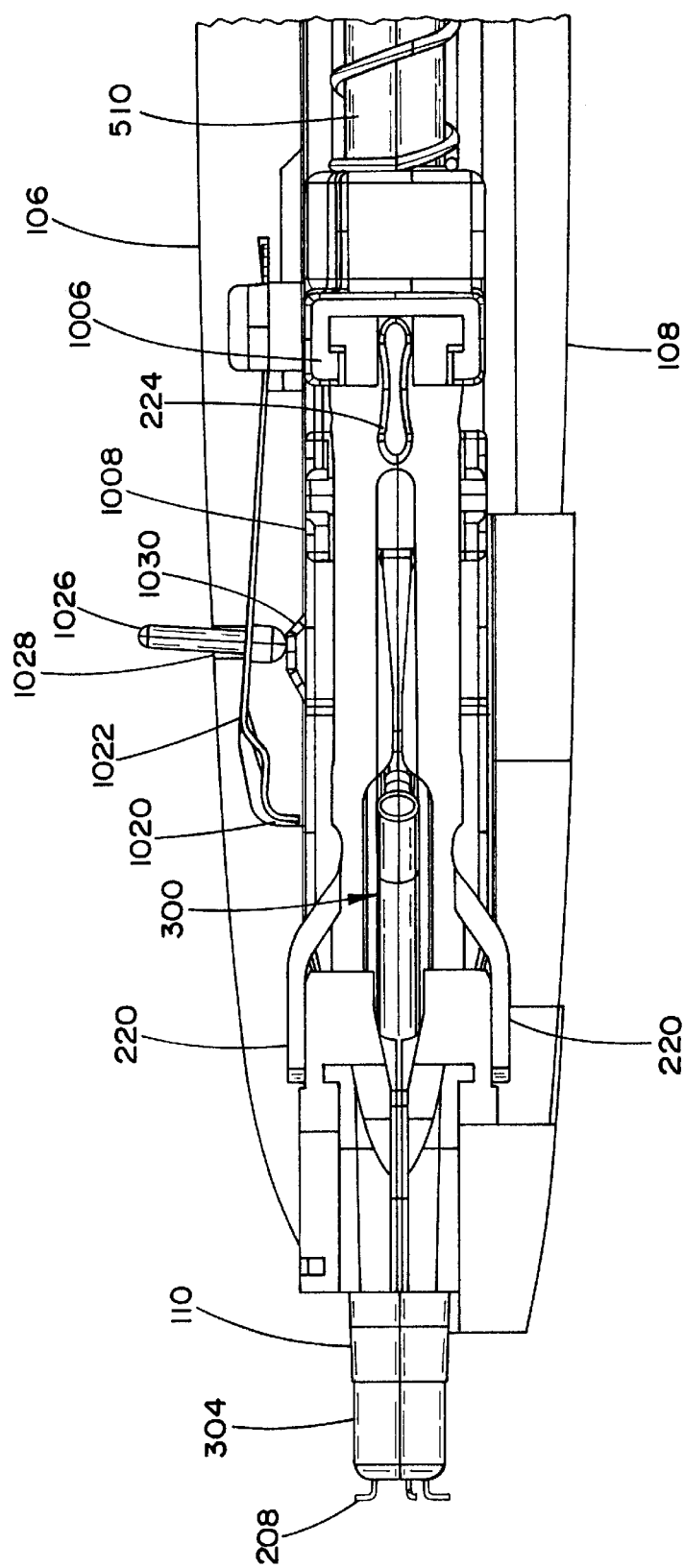
FIG. 16b illustrates a top view of the surgical device of FIG. 16a showing a corresponding position of the timing mechanism.

Referring now to FIGS. 16a and 16b, the cartridge pull plate 1006 is retracted distally a predetermined amount X while the contra pull plate 1008 is held stationary which in effect advances the contra 204 distally to fully expose the distal set of pins 208. The cartridge pull plate 1006 is retracted by turning the knob 500, which in turn turns the screw tube 510. After the cartridge pull plate 1006 is advanced the predetermined distance X, the pin 1026 rides over a cam 1030 to remove the distal end 1020 of the leaf spring 1022 from the first slot 1024. In this position, continued turning of the knob 500 retracts both the cartridge pull plate 1006 and the contra pull plate 1008.

Figure 17:
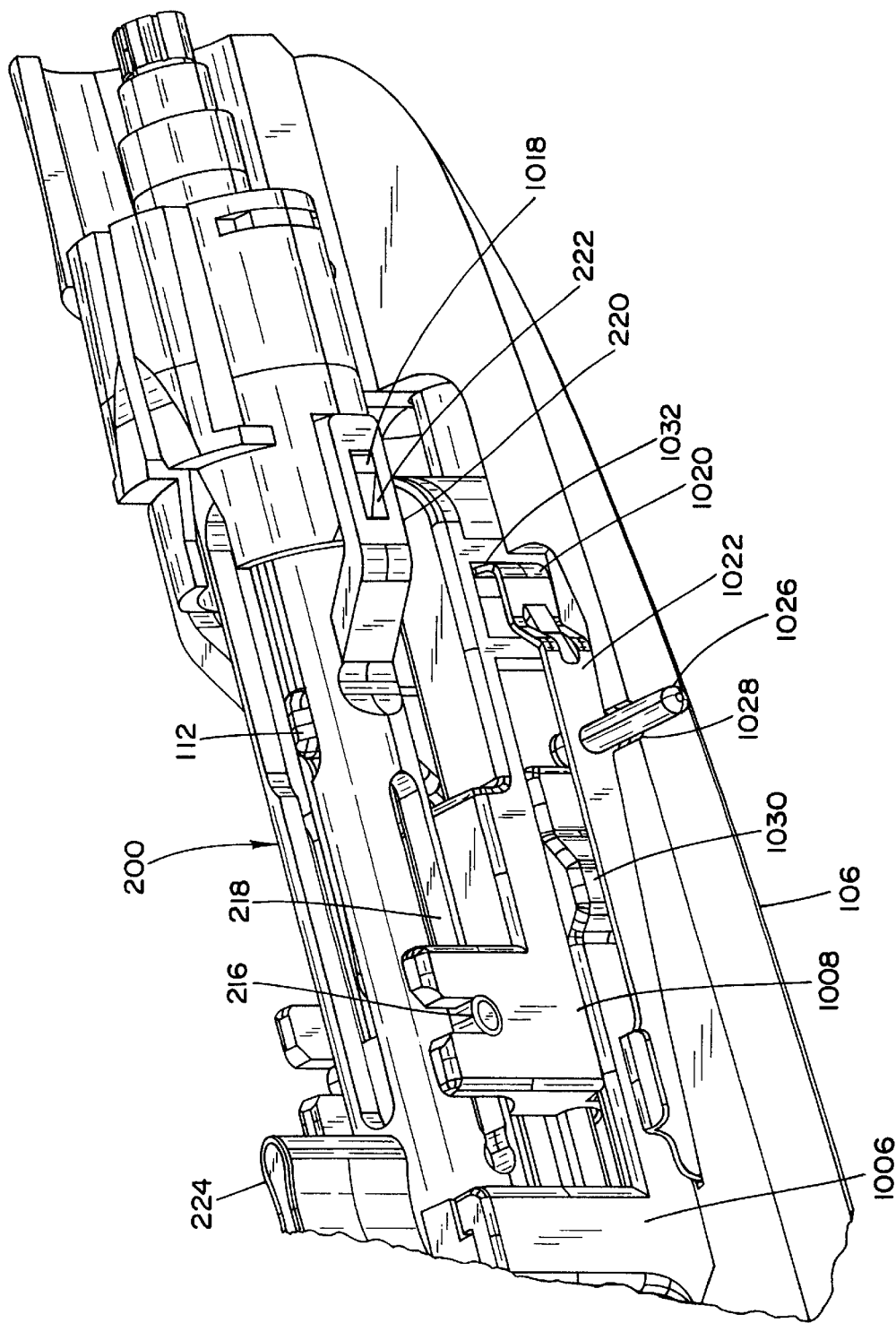
FIG. 17 illustrates an isometric view of a distal end of the surgical device where second hollow organ is deployed and the cartridge is about to split, FIG. 17 having a portion of the handle removed for clarity.
Figure 18:
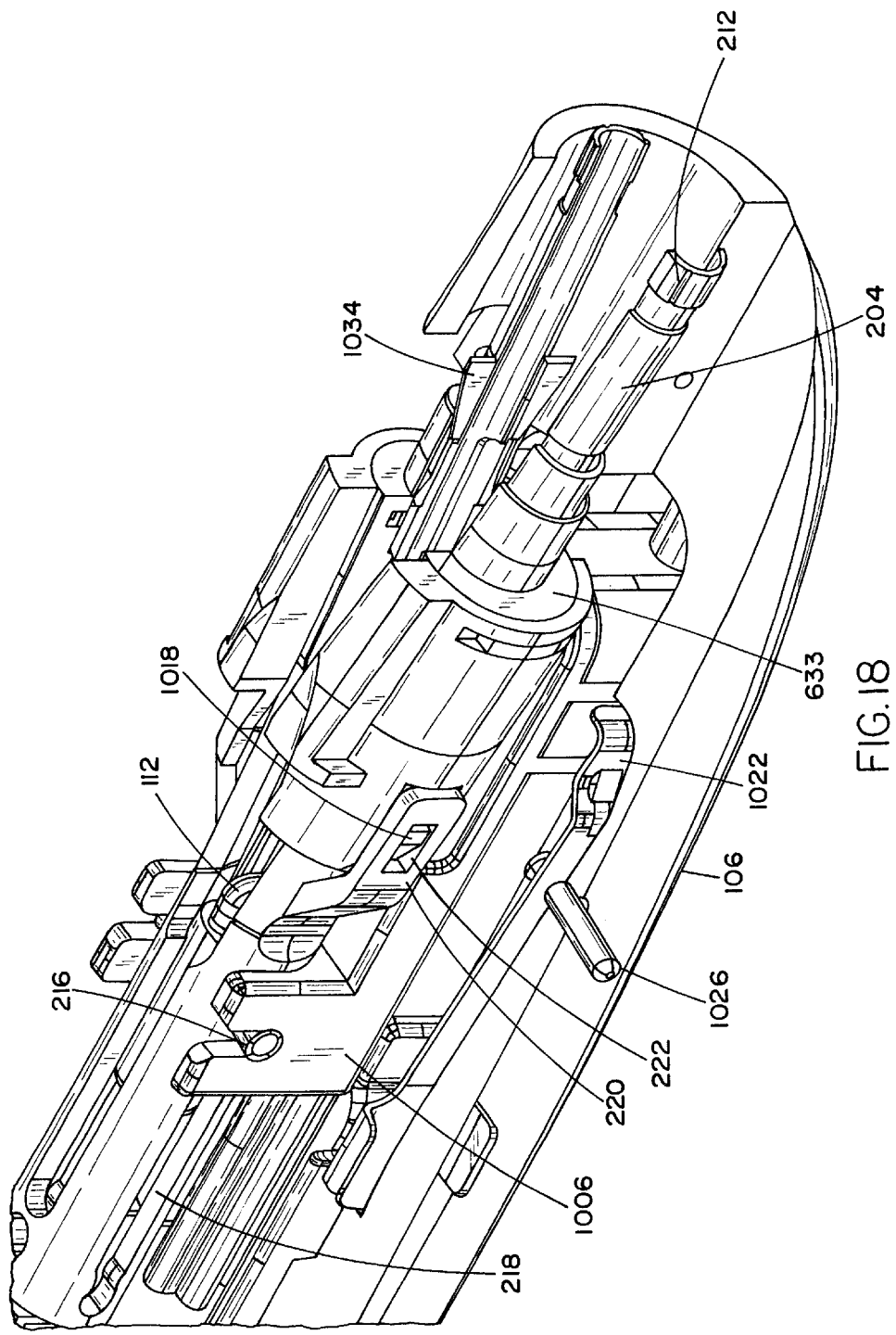
FIG. 18 illustrates an isometric view of a distal end of the surgical device where the cartridge is split.

Referring now to FIGS. 17 and 18, upon continued rotation of the knob 500, the pin 1026 moves past the cam 1030 and the distal end 1020 of the leaf spring 1022 engages a second slot 1032 in the contra pull plate 1008, thereby stopping its movement. Continued rotation of the knob 500 retracts only the cartridge pull plate 1006 relative to the contra pull plate 1006 and contra 204. Referring now to FIG. 18, a knife 1034 attached to the contra 204 is forced through the distal portion 234 of the slot 228 and eventually splits the cartridge body 202, seal 633, and nose piece 110 in half and separates the contra 204 to remove the restraint from the coupler body 210 and proximal set of pins 209 and to deploy the coupler 206 and second hollow organ 300 to create the anastomosis. The wedge 112 facilitates the splitting of the cartridge body 202 and contra 204.

Figure 19:
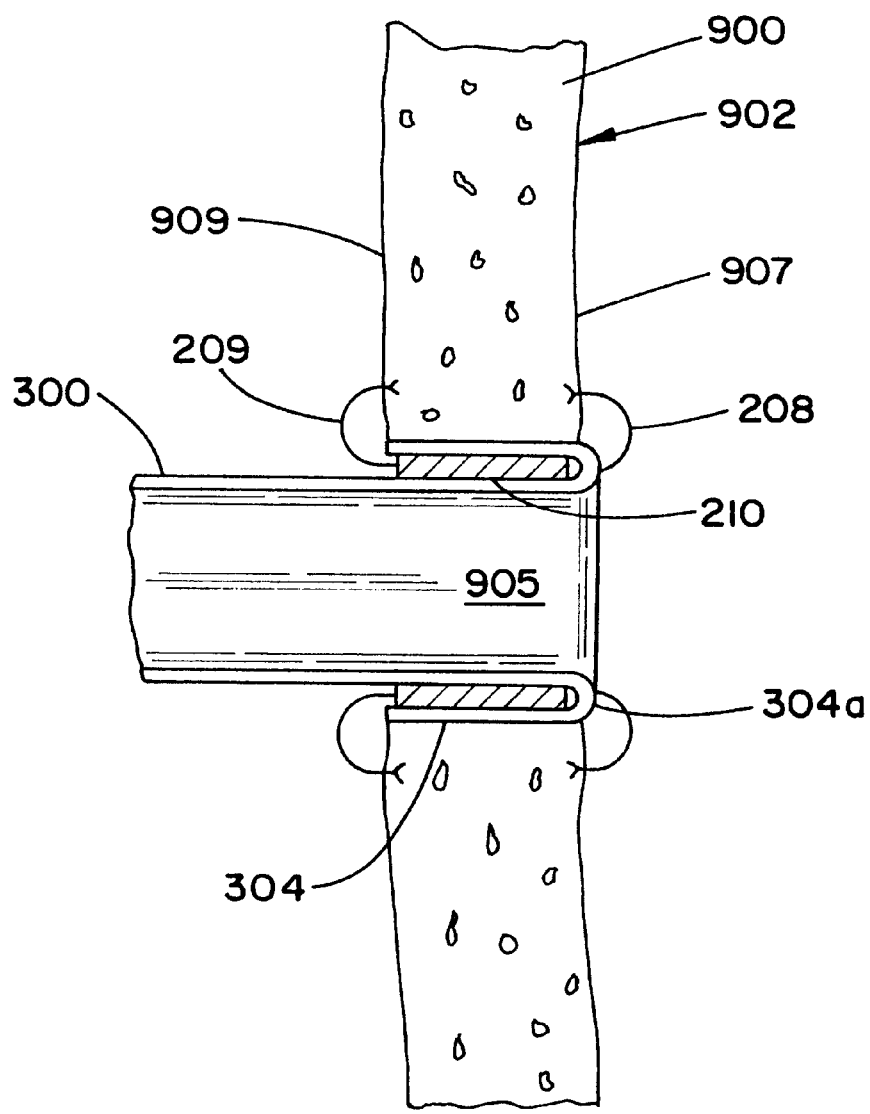
FIG. 19 illustrates a partial cross sectional view of a second hollow organ deployed in the wall of a first hollow organ.

Referring now to FIG. 19, after deployment, the coupler 206 expands radially to sandwich the everted portion of the second hollow organ between the inner surface of the hole 905 and the coupler body 210 to create a seal between the first and second hollow organs. The distal set of pins 208 pierce the turned over portion 304a of the everted second hollow organ 300 and lodge in an inner surface 907 of the wall 900 of the first hollow organ circumferentially about the hole 905. The proximal set of pins 209 are fully unrestrained and lodge in an outer surface 909 of the wall 900 of the first hollow organ 902 circumferentially about the hole 905.

Figure 20:
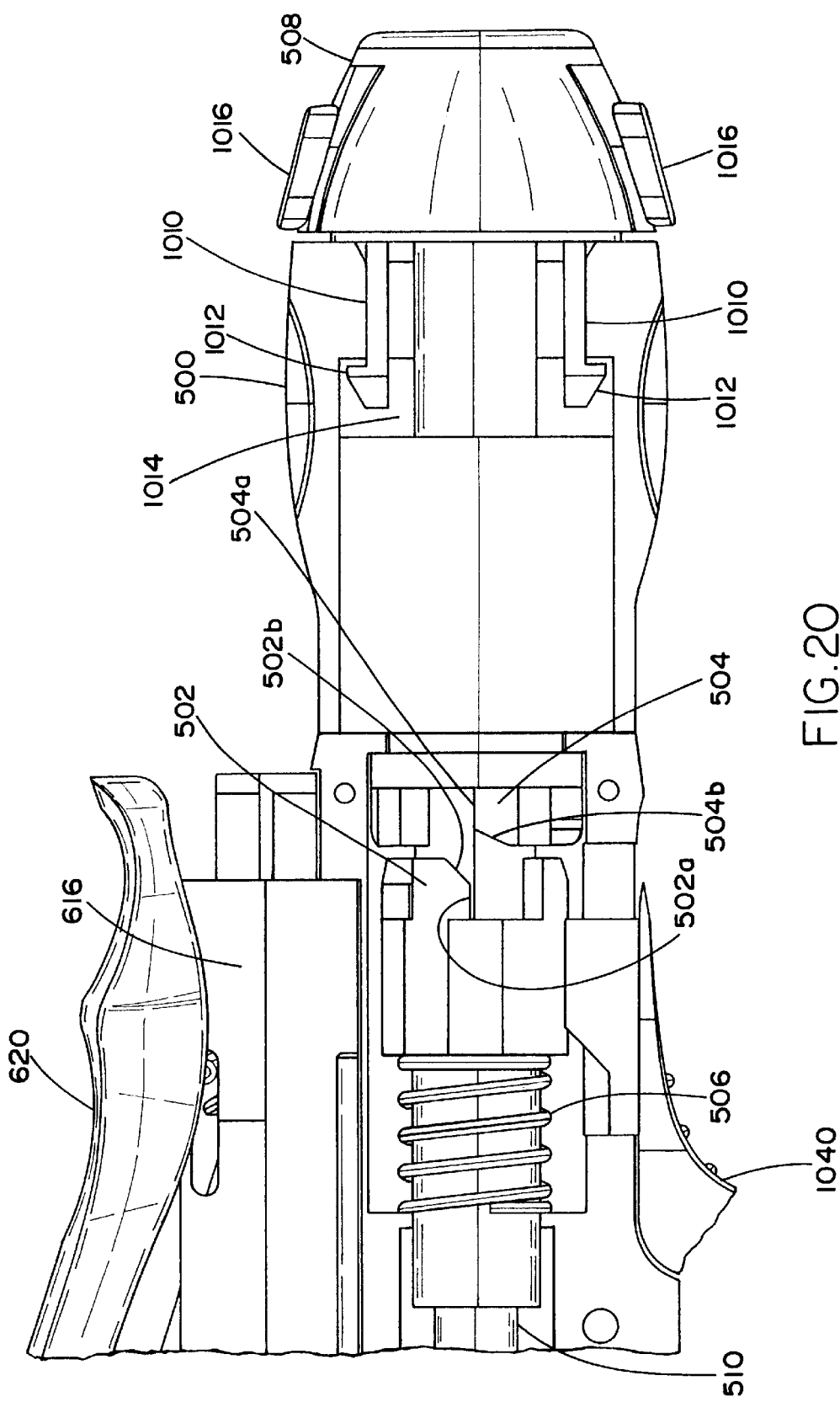
FIG. 20 illustrates a cross sectional view of a proximal end of the surgical instrument after deployment of the second hollow organ and being reset to an initial position for acceptance of another loaded cartridge.

Referring now to FIG. 20, to reset the surgical device 100 for creating further anastomosis, the split cartridge is removed and a reset button 1040 is advanced distally to totally disengage the gears 502, 504 allowing rotation of the knob 500 in the counterclockwise direction. The knob 500 is rotated until the cartridge and contra pull plates 1006, 1008 of the cradle 1000 abut one another. Furthermore, a new nose piece 110 and seal 633 are replaced and the tab buttons 1016 are depressed to disengage the hooked ends 1012 of the tabs 1010 with the cavity 1014 and the knob cap 508 is separated from the knob 500 and retracted proximally until the cradle 1000 is in position to be rotated into the cutting position. The punch 600 is then slid distally back into the cutting position with the punch point 612 retracted so as not to tear the seal 633 when it is eventually inserted into the nose 110. The device 100 is then ready to accept another loaded cartridge 200 and create another anastomosis. For instance, other harvested vessels can be anastomosed to the aorta or the distal end of the harvested vessel can be anastomosed around the blockage to the diseased coronary artery. Alternatively, the distal end of the harvested vessel can be hand sewn to the diseased coronary artery and the proximal end of the harvested vessel can be anastomosed to the aorta using the device 100 of the present invention without ripping the distal end free.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon attaches the proximal end of each graft vessel to the patient's aorta with the surgical devices of the present invention. The distal end may be attached to the diseased coronary artery, distal to the blockage or lesion, before or after the proximal end is attached to the aorta. Furthermore, the distal end may be sutured or also attached using the surgical devices of the present invention. The surgeon checks the bypass grafts for adequate blood flow in a conventional manner, and then completes the remainder of the operation in a conventional manner.

The veins used in the CABG procedure are harvested endoscopically using vein-harvesting instruments. Using these instruments, initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, ligation clips are applied, and the vessel is transected in order to remove the vein from the knee incision. Thee harvested vein is prepared for use as grafts in a conventional manner.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A surgical device for creating an anastomosis between first and second hollow organs, the device comprising:

a housing;

a punch slidingly disposed in the housing along a central axis for forming a hole in the first hollow organ;

a cartridge movably disposed in the housing between a position offset from the central axis and a position aligned with the central axis, the cartridge adapted to receive the second hollow organ and a coupler for coupling the first and second hollow organs loaded therein;

punch actuation means for sliding the punch between cutting and deploying positions, wherein while in the cutting position the punch is in position to form the hole in the first hollow organ and while in the deploying position, the punch is in position to permit the deployment of the second hollow organ;

cartridge actuation means for moving the cartridge between the cutting and deploying positions, wherein while in the cutting position the cartridge is in the position offset from the central axis and while in the deploying position, the cartridge is in the position aligned with the central axis; and deploying means for deploying the second hollow organ and coupler into the hole while the punch and cartridge are in the deploying position to create the anastomosis.

2. The device of claim 1, wherein the punch comprises:
a shaft disposed along the central axis; and
a punch tip disposed at a distal portion of the shaft and having a pointed surface for piercing the first hollow organ.

3. The device of claim 2, wherein the punch tip has a proximal edge for cutting a wall of the first hollow organ, the punch further having a grooved portion proximate to the punch tip for capturing a wall of the first hollow organ, the punch further comprising means for retracting the punch tip to sandwich the wall between the proximal edge and a portion of the housing and to sever the wall around a periphery of the proximal edge.

4. The device of claim 1, further comprising means for retracting the pointed surface of the punch tip into a lumen of the shaft.

5. The device of claim 1, wherein the cartridge further comprises a seal for sealing liquid in the first internal organ from entering the device.

6. The device of claim 5, wherein the cartridge further comprises a splitting means for splitting the cartridge and seal subsequent to deployment of the second hollow organ and coupler for facilitating release of the second hollow organ from the device.

7. The device of claim 1, wherein the coupler has pins for securing the second hollow organ to the hole of the first hollow organ, the pins being biased in a bent position, the cartridge further comprises retaining means for retaining the pins in a substantially straight position prior to deployment of the second hollow organ and coupler.

8. The device of claim 1, wherein the punch actuation means comprises:
a punch lever rotatably disposed on a shaft of the punch, wherein pulling the punch lever in the proximal direction moves the punch from the cutting position to the deploying position; and
retainer means for retaining the punch lever in the housing as it is pulled in the proximal direction.

9. The device of claim 8, wherein the punch actuation means comprises locking means for locking the punch lever and punch in the deploying position.

10. The device of claim 1, wherein the cartridge is rotatably disposed in the housing and wherein the cartridge actuation means comprises;
a cradle rotatably disposed in the housing for accepting the cartridge; and
a shaft connected to the housing upon which the cradle rotates.

11. The device of claim 10, wherein the cartridge actuation means further comprises a locking means for locking the cartridge in the deploying position.

12. The device of claim 10, wherein the cradle has orientation means for orienting the cartridge in a predetermined position in the housing.

13. The device of claim 1, wherein the coupler has pins for securing the second hollow organ to the hole of the first hollow organ, the pins being biased in a bent position, the cartridge further comprises retaining means for retaining pins in a substantially straight position prior to deployment of the second hollow organ and coupler, wherein the deploying means comprises;
means for pushing a distal end of the second hollow organ and the coupler into the hole of the first hollow organ; and
means for releasing the restraint on the pins thereby fixing the second hollow organ to the hole of the first hollow organ.

14. The device of claim 13, wherein the means for pushing the distal end of the second hollow organ and coupler into the hole of the first hollow organ comprises a shaft operatively connected to the cartridge for sliding the cartridge along the central axis such that the distal end of the second hollow organ protrudes from the housing and into the hole of the first hollow organ.

15. The device of claim 13, wherein the means for releasing the restraint on the pins comprises:
a screw tube rotatably disposed in the housing and operatively connected to the cartridge;
a knob connected to a distal end of the screw tube, wherein rotation of the knob releases the restraint on the pins.

16. The device of claim 13, further comprising a restraint means for restraining the rotation of the knob in the direction that releases the restraint on the pins.

17. The device of claim 16, further comprising a restraint release means for releasing the restraint and allowing the knob to be reset to an initial position for subsequent operations of the device.

18. The device of claim 1, wherein the first hollow organ is the aorta of the heart and the second hollow organ is a harvested vessel.

19. The device of claim 1, wherein the coupler is an anastomotic device having a set of pins on each of two ends, one of the sets of pins coupling the anastomotic device to a distal end of the second hollow organ and the other set of pins coupling the anastomotic device to a wall of the second hollow organ about the hole.

20. A method for creating an anastomosis between first and second hollow organs, the method comprising:
providing a punch slidingly disposed in a housing along a central axis;
providing a cartridge movably disposed in the housing between a position offset from the central axis and a position aligned with the central axis;
loading the second hollow organ and a coupler for coupling the first and second hollow organs into the cartridge;
sliding the punch distally to create a hole in a wall of the first hollow organ;
sliding the punch proximally to provide clearance for rotation of the cartridge into the position aligned with the central axis;
moving the cartridge from the axis offset from the central axis to the position aligned with the central axis; and
deploying the second hollow organ and coupler into the hole to create the anastomosis.

21. The method of claim 20, wherein the punch comprises a shaft disposed along the central axis; and a punch tip disposed at a distal portion of the shaft and having a pointed surface for piercing the first hollow organ, the method further comprising retracting the pointed surface of the punch tip into a lumen of the shaft.

22. The method of claim 21, wherein the punch tip has a proximal edge for cutting the wall of the first hollow organ, the punch further having a grooved portion proximate to the punch tip, the method further comprising:
capturing the wall of the first hollow organ in the grooved portion; and
retracting the punch tip to sandwich the wall between the proximal edge and a portion of the housing to sever the wall around a periphery of the proximal edge.

23. The method of claim 20, further comprising sealing liquid in the first internal organ from entering the device.

24. The method of claim 23, further comprising splitting the cartridge and seal subsequent to deployment of the second hollow organ and coupler for facilitating release of the second hollow organ from the device.

25. The method of claim 20, wherein the coupler has pins for securing the second hollow organ to the hole of the first hollow organ, the pins being biased in a bent position, the method further comprising retaining the pins in a substantially straight position prior to deployment of the second hollow organ and coupler.

26. The method of claim 25, further comprising;

pushing a distal end of the second hollow organ and the coupler into the hole of the first hollow organ; and releasing the restraint on the pins thereby fixing the second hollow organ to the hole of the first hollow organ.

27. The method of claim 26, wherein a screw tube is rotatably disposed in the housing and operatively connected to the cartridge, wherein the releasing comprises rotating a knob connected to a distal end of a screw tube to release the restraint on the pins.

28. The method of claim 27, further comprising restraining the rotation of the knob in the direction that releases the restraint on the pins.

29. The method of claim 28, further comprising releasing the restraint and allowing the knob to be reset to an initial position for subsequent operations of the device.

30. The method of claim 25, further comprising preventing the loading of the cartridge into the housing unless a distal set of the pins are pierced through an everted portion of the second hollow organ by at least partly releasing the retaining of the pins.

31. A surgical device for creating an anastomosis between first and second hollow organs, the device comprising:

a housing with a central axis;

a punch slidingly disposed in the housing for forming a hole in the first hollow organ;

a cartridge movably disposed in the housing between a cutting position and a deploying position, the cartridge adapted to receive the second hollow organ and a coupler for coupling the first and second hollow organs loaded therein;

punch actuation means for sliding the punch between the cutting and deploying positions, wherein while in the cutting position the punch is in position to form the hole in the first hollow organ and while in the deploying position, the punch is in position to permit the deployment of the second hollow organ;

cartridge actuation means for moving the cartridge between the cutting and deploying positions, wherein while in the cutting position, the cartridge is in a position offset from the central axis to permit the punch to form the hole in the first hollow organ and while in the deploying position, the cartridge is in position to deploy the second hollow organ; and deploying means for deploying the second hollow organ and coupler into the hole while the punch and cartridge are in the deploying position to create the anastomosis.

* * * * *